US009316586B2

(12) United States Patent
Maltezos et al.

(10) Patent No.: US 9,316,586 B2
(45) Date of Patent: *Apr. 19, 2016

(54) APPARATUS FOR THERMAL CYCLING

(75) Inventors: George Maltezos, Fort Salonga, NY (US); Matthew Johnston, Woodbridge, CA (US); David Goodwin, Pasadena, CA (US); Axel Scherer, Laguna Beach, CA (US); Christopher I. Walker, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 3 days.

This patent is subject to a terminal disclaimer.

(21) Appl. No.: 13/417,121

(22) Filed: Mar. 9, 2012

(65) Prior Publication Data
US 2012/0171678 A1 Jul. 5, 2012

Related U.S. Application Data

(63) Continuation of application No. 11/750,326, filed on May 17, 2007, now Pat. No. 8,232,091.

(60) Provisional application No. 60/801,178, filed on May 17, 2006, provisional application No. 60/832,492, filed on Jul. 21, 2006, provisional application No. 60/873,084, filed on Dec. 6, 2006, provisional application No. 60/873,172, filed on Dec. 6, 2006.

(51) Int. Cl.
*G01N 21/64* (2006.01)
*B01L 7/00* (2006.01)
*B01L 3/00* (2006.01)

(52) U.S. Cl.
CPC .......... *G01N 21/645* (2013.01); *B01L 3/50851* (2013.01); *B01L 7/52* (2013.01);

(Continued)

(58) Field of Classification Search
CPC ................................................ B01L 2300/185
See application file for complete search history.

(56) References Cited

U.S. PATENT DOCUMENTS 2,962,268 A 11/1960 Soltermann
4,683,202 A 7/1987 Mullis
(Continued)

FOREIGN PATENT DOCUMENTS

EP 0 363 143 4/1990
EP 0363143 4/1990
(Continued)

OTHER PUBLICATIONS

Chemicool web page for mercury [online] [retrieved on Jan. 25, 2010] retrieved from http://www.chemicool.com/elements/mercury. html (5 pages).

(Continued)

*Primary Examiner* — Samuel Woolwine
(74) *Attorney, Agent, or Firm* — Knobbe, Martens, Olson & Bear, LLP

(57) ABSTRACT

This invention provides a system for performing PCR, and real time PCR in particular, with great speed and specificity. The system employs a heat block containing a liquid composition to rapidly transfer heat to and from reaction vessels. The system makes use of the reflective properties of the liquid metal to reflect signal from the PCR into the vessel and out the top. In this way, the signal can be measured by an optical assembly in real time without removing the vessels from the heat block.

27 Claims, 17 Drawing Sheets

(52) U.S. Cl.
CPC .............. *B01L 3/50853* (2013.01); *B01L 7/54* (2013.01); *B01L 2200/147* (2013.01); *B01L 2300/0829* (2013.01); *B01L 2300/0838* (2013.01); *B01L 2300/12* (2013.01); *B01L 2300/168* (2013.01); *B01L 2300/185* (2013.01); *B01L 2300/1822* (2013.01); *B01L 2300/1827* (2013.01); *B01L 2300/1861* (2013.01)

(56) References Cited

U.S. PATENT DOCUMENTS

| | | | |
|---|---|---|---|
| 4,824,329 A | 4/1989 | Yamamoto et al. | |
| 5,079,352 A | 1/1992 | Gelfand et al. | |
| 5,210,015 A | 5/1993 | Gelfand et al. | |
| 5,310,652 A | 5/1994 | Gelfand et al. | |
| 5,314,809 A | 5/1994 | Erlich et al. | |
| 5,322,770 A | 6/1994 | Gelfand | |
| 5,323,008 A | 6/1994 | Studholme et al. | |
| 5,401,465 A | 3/1995 | Smethers et al. | |
| 5,407,800 A | 4/1995 | Gelfand et al. | |
| 5,455,175 A | 10/1995 | Wittwer et al. | |
| 5,487,972 A | 1/1996 | Gelfand et al. | |
| 5,508,197 A | 4/1996 | Hansen et al. | |
| 5,538,848 A | 7/1996 | Livak et al. | |
| 5,552,580 A | 9/1996 | Pfost et al. | |
| 5,618,711 A | 4/1997 | Gelfand et al. | |
| 5,643,535 A | 7/1997 | Smethers et al. | |
| 5,656,493 A | 8/1997 | Mullis et al. | |
| 5,677,152 A | 10/1997 | Birch et al. | |
| 5,716,583 A | 2/1998 | Smethers et al. | |
| 5,773,258 A | 6/1998 | Birch et al. | |
| 5,789,224 A | 8/1998 | Gelfand et al. | |
| 5,795,547 A | 8/1998 | Moser et al. | |
| 5,871,908 A | 2/1999 | Henco et al. | |
| 5,928,907 A | 7/1999 | Woudenberg et al. | |
| 5,935,522 A | 8/1999 | Swerdlow et al. | |
| 5,972,716 A | 10/1999 | Ragusa et al. | |
| 5,994,056 A | 11/1999 | Higuchi | |
| 6,015,674 A | 1/2000 | Woudenberg et al. | |
| 6,127,155 A | 10/2000 | Gelfand et al. | |
| 6,140,613 A | 10/2000 | Tsuno | |
| 6,144,448 A | 11/2000 | Mitoma | |
| 6,171,785 B1 | 1/2001 | Higuchi | |
| 6,174,670 B1 | 1/2001 | Wittwer et al. | |
| 6,232,079 B1 | 5/2001 | Wittwer et al. | |
| 6,245,514 B1 | 6/2001 | Wittwer et al. | |
| 6,303,305 B1 | 10/2001 | Wittwer et al. | |
| 6,472,186 B1 | 10/2002 | Quintanar et al. | |
| 6,503,720 B2 | 1/2003 | Wittwer et al. | |
| 6,533,255 B1 | 3/2003 | Mitsuhashi et al. | |
| 6,569,627 B2 | 5/2003 | Wittwer et al. | |
| 6,665,186 B1 | 12/2003 | Calmidi et al. | |
| 6,677,151 B2 | 1/2004 | Sandell | |
| 6,691,041 B2 | 2/2004 | Sagner et al. | |
| 6,708,501 B1 | 3/2004 | Ghoshal et al. | |
| 6,730,501 B2 | 5/2004 | Eyre | |
| 6,744,502 B2 | 6/2004 | Hoff et al. | |
| 6,746,864 B1 | 6/2004 | McNeil et al. | |
| 6,787,338 B2 | 9/2004 | Wittwer et al. | |
| 6,800,452 B1 | 10/2004 | McNeil et al. | |
| 6,814,934 B1 | 11/2004 | Higuchi | |
| 6,818,437 B1 | 11/2004 | Gambini et al. | |
| 6,825,927 B2 | 11/2004 | Goldman et al. | |
| 6,852,986 B1 | 2/2005 | Lee et al. | |
| 6,873,417 B2 | 3/2005 | Bahatt et al. | |
| 6,928,860 B1 | 8/2005 | Hildebrandt et al. | |
| 6,982,166 B2 | 1/2006 | Sandell | |
| 7,081,226 B1 | 7/2006 | Wittwer et al. | |
| 7,109,495 B2 | 9/2006 | Lee et al. | |
| 7,122,799 B2 | 10/2006 | Hsieh et al. | |
| 7,131,286 B2 | 11/2006 | Ghoshal et al. | |
| 7,141,370 B2 | 11/2006 | Hassibi et al. | |
| 7,148,043 B2 | 12/2006 | Kordunsky et al. | |
| 7,183,103 B2 | 2/2007 | Gambini et al. | |
| 7,238,321 B2 | 7/2007 | Wittwer et al. | |
| 7,273,749 B1 | 9/2007 | Wittwer et al. | |
| 7,315,376 B2 | 1/2008 | Bickmore, Jr. et al. | |
| 7,373,253 B2 | 5/2008 | Eyre | |
| 7,387,887 B2 | 6/2008 | Wittwer et al. | |
| 7,387,891 B2 | 6/2008 | Boege et al. | |
| 7,407,798 B2 | 8/2008 | Oldham et al. | |
| 7,410,793 B2 | 8/2008 | Boege et al. | |
| 7,414,724 B2 | 8/2008 | Eckert et al. | |
| 7,427,380 B2 | 9/2008 | McNeil et al. | |
| 7,582,429 B2 | 9/2009 | Wittwer et al. | |
| 2001/0046050 A1 | 11/2001 | Hoyt | |
| 2001/0049134 A1* | 12/2001 | Lee et al. | 435/286.1 |
| 2002/0006619 A1 | 1/2002 | Cohen et al. | |
| 2002/0030044 A1* | 3/2002 | Brown | 219/386 |
| 2002/0086417 A1 | 7/2002 | Chen | |
| 2002/0164114 A1 | 11/2002 | Golub et al. | |
| 2002/0192755 A1 | 12/2002 | Francis et al. | |
| 2003/0138244 A1 | 7/2003 | Long et al. | |
| 2003/0150957 A1 | 8/2003 | Thomas | |
| 2003/0157498 A1 | 8/2003 | Eyre et al. | |
| 2003/0157721 A1 | 8/2003 | Turner | |
| 2003/0165867 A1 | 9/2003 | Eyre et al. | |
| 2003/0224434 A1 | 12/2003 | Wittwer et al. | |
| 2003/0233008 A1 | 12/2003 | Ooms et al. | |
| 2004/0009586 A1* | 1/2004 | Oldham et al. | 435/287.2 |
| 2004/0014202 A1 | 1/2004 | King et al. | |
| 2004/0023229 A1 | 2/2004 | Rigler | |
| 2004/0025210 P1 | 2/2004 | Beineke | |
| 2004/0076952 A1 | 4/2004 | Kawai | |
| 2004/0142459 A1 | 7/2004 | Sandell | |
| 2004/0178357 A1 | 9/2004 | King | |
| 2004/0214315 A1 | 10/2004 | Saluz et al. | |
| 2004/0222384 A1* | 11/2004 | Lee et al. | 250/458.1 |
| 2004/0224117 A1 | 11/2004 | Kordunsky et al. | |
| 2004/0253614 A1 | 12/2004 | Yonekawa et al. | |
| 2005/0084957 A1* | 4/2005 | Atwood et al. | 435/304.1 |
| 2005/0133724 A1 | 6/2005 | Hsieh et al. | |
| 2005/0136448 A1 | 6/2005 | Hartel et al. | |
| 2005/0202484 A1* | 9/2005 | Moore | C12Q 1/6883 435/6.11 |
| 2005/0221367 A1 | 10/2005 | Tran | |
| 2005/0279949 A1 | 12/2005 | Oldham et al. | |
| 2006/0019253 A1 | 1/2006 | Wittwer et al. | |
| 2006/0029965 A1 | 2/2006 | Wittwer | |
| 2006/0048518 A1 | 3/2006 | Bell | |
| 2006/0065652 A1 | 3/2006 | Brown | |
| 2006/0105433 A1 | 5/2006 | Bickmore et al. | |
| 2006/0157223 A1 | 7/2006 | Gelorme et al. | |
| 2006/0289786 A1 | 12/2006 | Taylor et al. | |
| 2007/0110634 A1 | 5/2007 | Heimberg et al. | |
| 2007/0114444 A1 | 5/2007 | Reid et al. | |
| 2008/0038163 A1 | 2/2008 | Boege et al. | |
| 2008/0050781 A1 | 2/2008 | Oldham et al. | |
| 2008/0124722 A1 | 5/2008 | Dromaretsky et al. | |
| 2008/0194014 A1 | 8/2008 | Young et al. | |
| 2009/0176282 A1 | 7/2009 | Sandell | |

FOREIGN PATENT DOCUMENTS

| | | |
|---|---|---|
| EP | 0 488 769 | 6/1992 |
| EP | 0512334 B1 | 11/1992 |
| EP | 775298 A1 | 2/1996 |
| EP | 0236069 B1 | 5/1997 |
| EP | 1335028 A2 | 8/2003 |
| EP | 1335028 A3 | 8/2003 |
| EP | 1335028 B1 | 8/2003 |
| EP | 1470253 A2 | 8/2003 |
| EP | 725929 | 11/2003 |
| EP | 1157744 B1 | 3/2004 |
| EP | 1880175 A2 | 11/2006 |
| EP | 1943655 A2 | 3/2007 |
| EP | 1228357 B1 | 5/2008 |
| JP | 60046055 A | 3/1985 |
| JP | 03288552 A * | 12/1991 |
| JP | 7185363 | 7/1995 |
| JP | 07185363 A | 7/1995 |
| JP | 2000 511435 | 9/2000 |
| JP | 2000 512138 | 9/2000 |
| JP | 2002 119847 | 4/2002 |

(56) References Cited

FOREIGN PATENT DOCUMENTS

| JP | 2004 028775 | 1/2004 |
|---|---|---|
| JP | 2005 117987 | 5/2005 |
| WO | WO 00/69561 | 11/2000 |
| WO | WO 01/24930 | 4/2001 |
| WO | 2004/105947 | 12/2004 |
| WO | WO 2004 105947 | 12/2004 |
| WO | WO 2005 051065 A2 | 6/2005 |
| WO | WO 2005 051065 A3 | 10/2005 |
| WO | WO 2005 096320 A2 | 10/2005 |
| WO | WO 2005 096320 A3 | 4/2006 |
| WO | WO 2007 150043 A2 | 12/2007 |

OTHER PUBLICATIONS

CRC Handbook of Chemistry and Physics [online] [retrieved on Jul. 6, 2011] retrieved from http://www.hbcpnetbase.com/ (2pages total).

Department of Homeland Security—Guide for the selection of biological agent detection equipment for emergency first responders. Guide 101-04. vol. II. Mar. 2005 (324 pages).

Gallium Element Facts [online] [retrieved on Jan. 21, 2011] retrieved from http://www.chemicool.com/elements/gallium.html.

Gallium Element Facts, http://www.chemicool.com/elements/gallium.html (accessed: Jun. 13, 2011).

Heid et al., "Real time quantitative PCR," *Genome Research* 6:986-994 (1996).

International Search Report dated Jan. 16, 2008 for International Patent Application No. PCT/US07/69197.

Mercury Element Facts, http://www.chemicool.com/elements/mercury.htm (accessed: Jun. 13, 2011).

Morrison et al., "Solution-Phase Detection of Polynucleotides Using Interacting Fluorescent Labels and Competitive Hybridization," *Analytical Biochem*. 183:231-244 (1989).

Schoder et al. Novel approach for assessing performance of peR cyclers used for diagnostic testing. *J Clin Microbiol*. 2005; 43(6):2724-8.

The Engineering Toolbox [online][retrieved on Dec. 4, 2011] retrieved from http://www.engineeringtoolbox.com/thermalconductivity-d_429.html.

Voight et al. A review of ammonia-mediated buoyancy in squids (Cephalopoda: Teuthoidea). Mar. Fresh. Behav. Physiol., vol. 25, pp. 193-203 (1994).

* cited by examiner

US 9,316,586 B2

APPARATUS FOR THERMAL CYCLING

CROSS-REFERENCE

This application is a continuation of U.S. patent application Ser. No. 11/750,326, filed May 17, 2007, which claims the benefit of U.S. Provisional Application No. 60/801,178 filed May 17, 2006, U.S. Provisional Application No. 60/832,492, filed Jul. 21, 2006, U.S. Provisional Application No. 60/873,084 filed Dec. 6, 2006, and U.S. Provisional Application No. 60/873,172 filed Dec. 6, 2006. The disclosures of each of these applications are hereby incorporated by reference in their entireties.

FEDERAL SUPPORT STATEMENT

This invention was made with government support under HG0022644 awarded by National Institutes of Health and HR0011-0401-0032 awarded by Defense Advanced Research Projects Agency. The government has certain rights in the invention.

BACKGROUND OF THE INVENTION

Invented in 1983 by Kary Mullis, PCR is recognized as one of the most important scientific developments of the twentieth century. PCR has revolutionized molecular biology through vastly extending the capability to identify and reproduce genetic materials such as DNA. Nowadays PCR is routinely practiced in medical and biological research laboratories for a variety of tasks, such as the detection of hereditary diseases, the identification of genetic fingerprints, the diagnosis of infectious diseases, the cloning of genes, paternity testing, and DNA computing. The method has been automated through the use of thermal stable DNA polymerases and a machine commonly referred to as "thermal cycler."

The conventional thermal cycler has several intrinsic limitations. Typically a conventional thermal cycler contains a metal heating block to carry out the thermal cycling of reaction samples. Because the instrument has a large thermal mass and the sample vessels have low heat conductivity, cycling the required levels of temperature is inefficient. The ramp time of the conventional thermal cycler is generally not rapid enough and inevitably results in undesired non-specific amplification of the target sequences. The suboptimal performance of a conventional thermal cycler is also due to the lack of thermal uniformity widely acknowledged in the art. Furthermore, the conventional real-time thermal cycler system carries optical detection components that are bulky and expensive. Mitsuhashi et al. (U.S. Pat. No. 6,533,255) discloses a liquid metal PCR thermal cycler.

There thus remains a considerable need for an alternative thermal cycler design. A desirable device would allow (a) rapid and uniform transfer of heat to effect a more specific amplification reaction of nucleic acids; and/or (b) real-time monitoring of the progress of the amplification reaction in real time. The present invention satisfies these needs and provides related advantages as well.

SUMMARY OF THE INVENTION

In one aspect this invention provides a method of performing PCR comprising: a) performing PCR in a sample vessel and generating a signal in the sample vessel indicating the course of the PCR, wherein substantially all said signal is reflected back into said sample vessel, wherein substantially all the signal is detected from said sample vessel from a discrete location; and b) measuring the signal emitted from the discrete location of the sample vessel. In one embodiment the method comprises measuring the signal over a plurality of PCR cycles in real time. In another embodiment the sample vessel comprises a wall transparent to the signal and at least part of the wall is immersed in a liquid composition that reflects substantially all the signal striking the liquid composition. In another embodiment the liquid composition comprises a metal or metal alloy. In another embodiment the signal is generated by a label or dye. In another embodiment said sample vessel comprises a material that reflects substantially all said signal in said sample In another embodiment said sample vessel is comprised of a metal. In another embodiment said sample vessel comprises a reflective material. In another embodiment said sample vessel is separated from said liquid composition by a receptacle.

In another aspect this invention provides a method of performing PCR comprising: a) performing PCR of a target nucleotide sequence in a reaction mixture under conditions wherein: (i) the rate of temperature change between primer extension and duplex dissociation and between primer annealing and primer extension is more than 10.5° C. per second (ii) said PCR is conducted in a heat block comprising sample vessels, comprising temperature variance of less than 0.5° C. within a sample vessel; and b) monitoring amplification of the target nucleotide sequence in real time. In one embodiment said heat block comprises a liquid composition. In another embodiment said method of performing PCR further comprises a temperature variance of less than 0.5° C. as measured between two or more wells in said heat block. In another embodiment said temperature variance is 0.01° C. as measured between two or more wells in said heat block. In another embodiment said heat block is a swap block. In another embodiment the rate of temperature change is effected by: (1) putting a sample vessel containing the reaction mixture in thermal contact with a liquid composition having a heat transfer coefficient of at least 0.1 W/m*K; wherein the temperature of the liquid composition controls the temperature of the reaction mixture. In another embodiment the temperature uniformity is maintained by inducing movement of the liquid composition.

In another aspect this invention provides a method of performing PCR comprising: conducting PCR in a thermal cycler which modulates sample temperature by more than 5° C. per second; wherein said thermal cycler temperature is regulated by a liquid composition in heat block with a liquid tight seal; wherein said liquid composition comprises a heat transfer coefficient of at least 0.1 W/m*K. In one embodiment said thermal cycler provides ramp rates of at least about 10° C. per second. In another embodiment said thermal cycler provides well-to-well and sample temperature uniformity of at least about 0.01 to 0.1° C. In another embodiment said heat block has a temperature variance is 0.01° C. as measured between two or more wells in said heat block. In another embodiment said liquid composition is contained within a heat block. In another embodiment said heat block is a swap block.

In another aspect this invention provides a method of performing PCR comprising; conducting PCR in a thermal cycler which modulates sample temperature sufficiently to allow detecting amplification in real time at a signal index of at least 3, wherein said detection is via a non-specific nucleic acid label, wherein said thermal cycler modulates sample temperature by more than 10° C. per second.

In another aspect this invention provides a method for performing real-time PCR comprising: a) performing a PCR reaction of a target nucleotide sequence in a reaction mixture under conditions wherein the rate of temperature change between primer extension and duplex dissociation and between primer annealing and primer extension in the reaction mixture is at least 5° C. per second, wherein said PCR reaction is in thermal contact with a liquid composition having heat transfer coefficient of at least 0.1 W/m*K; and b) monitoring the PCR in real time. In one embodiment said monitoring comprises: a) performing PCR in a sample vessel and generating signal in the sample vessel indicating the course of the PCR, wherein the signal is emitted from the sample vessel substantially from a discrete location; and b) measuring the signal emitted from the discrete location of the sample vessel. In another embodiment said rate of temperature increase in the reaction mixture is at least 40° C. per second. In another embodiment said temperature change is regulated by a Peltier element.

In another aspect this invention provides a method for performing real-time PCR comprising: a) cycling the temperature of the PCR reaction mixture between temperatures for duplex dissociation, primer annealing and primer extension for a plurality of cycles, wherein each cycle is no more than five seconds; wherein said temperatures are modulated by a liquid composition sealed in a thermal cycler; b) monitoring the course of PCR in the sample vessel in real time over a plurality of cycles. In one embodiment the method further comprises before step (a): placing a closed end of a sample vessel containing the PCR reaction mixture into thermal contact with a liquid composition that is liquid above 60° C. and that has a heat transfer coefficient of at least 0.1 W/m*K, whereby the temperature of the liquid composition controls the temperature of the PCR reaction mixture 30. In another embodiment said liquid composition reflects substantially all light inside the sample vessel. In another embodiment said monitoring is performed by measuring signal emitted from the top or bottom of the sample vessel. In another embodiment each cycle is no more than three seconds. In another embodiment said sample vessel comprises a reflective surface. In another embodiment said sample vessel is further covered with a cap. In another embodiment said cap is capable of absorbing heat from or being cooled by said liquid composition.

In another aspect this invention provides a method for conducting real time PCR comprising providing a thermal cycler comprising a liquid composition in thermal contact with PCR sample vessels; wherein said liquid composition modulates in temperature thus regulating reaction temperatures in the sample vessels, wherein a detectable signal is emitted from said sample vessels; and detecting said signal via an optical assembly comprising a light emitter and optical detector. In one embodiment said optical assembly comprises a pin photodiode CCD imager, a CMOS imager, a line scanner, a photodiode, a phototransistor, a photomultiplier or an avalanche photodiode. In another embodiment said sample vessel is further covered with a cap. In another embodiment said cap is capable of absorbing heat from or being cooled by said liquid composition.

In another aspect this invention provides an apparatus comprising: a) a temperature control assembly comprising a container containing a liquid composition that is liquid above 60° C. and that has a thermal conductivity of at least 0.1 W/m*K, said container having at least one aperture, each aperture adapted to receive a closed end of an sample vessel, wherein a sample vessel received into the aperture is placed in thermal contact with the liquid composition whereby the temperature of the liquid composition controls the temperature of a liquid sample in the sample vessel and wherein the liquid composition is capable of reflecting substantially all light inside the sample vessel; b) an optical assembly capable of detecting said light inside the sample vessel from a discrete location on said sample vessel; and c) a control assembly that controls the temperature of the liquid composition and the operation of the optical assembly. In one embodiment the liquid composition comprises gallium, a gallium-indium alloy or alloy comprising gallium, indium, rhodium, silver, zinc, tin or stannous. In another embodiment said temperature controller comprises a Peltier element. In another embodiment said temperature controller comprises resistive wire in thermal contact with the liquid composition. In another embodiment said temperature controller comprises means to cycle the temperature of the liquid composition between temperatures for duplex dissociation, primer annealing and primer extension appropriate for PCR. In another embodiment said thermal cycler further comprises means for circulating current in the liquid composition. In another embodiment said optical assembly comprises a light emitter and optical detector. In another embodiment said apparatus further comprises a sample preparation station comprising means to add reagents to sample vessels. In another embodiment said apparatus further comprises a means for moving the sample vessels into the apertures. In another embodiment said apparatus further comprises a digital computer that controls the thermal cycler, the optical assembly and the sample preparation station.

In another aspect this invention provides a system for performing real time PCR comprising: a) a thermal cycler comprising a liquid composition and means to engage a sample vessel and put said vessel in thermal contact with the composition; and b) an optical assembly comprising a light emitter and optical detector that directs light into an engaged sample vessel and detects light emitted from an engaged sample vessel. In one embodiment said liquid composition comprises a metal or metal alloy. In another embodiment said liquid composition comprises gallium. In another embodiment said signals emitted are from a removable cap of said sample vessel. In another embodiment said liquid composition is separated from said sample vessel by a receptacle. In another embodiment said receptacle is transparent or translucent. In another embodiment said system comprises a Peltier element. In another embodiment said thermal cycler further comprises a motor operatively connected to a fan and stir bar. In another embodiment said fan and stir bar are connected coaxially to said motor. In another embodiment said thermal cycler further comprises a resistive wire for thermal regulation of said liquid composition. In another embodiment said liquid composition is sealed in a closed barrier, wherein said barrier comprises a surface with receptacles into which said sample vessels are placed. In another embodiment said liquid composition directly contacts said sample vessels. In another embodiment said optical assembly comprises a PIN photodiode, CCD imager, a CMOS imager, a line scanner, a photodiode, a phototransistor, a photomultiplier or an avalanche photodiode.

In another aspect this invention provides an apparatus comprising a) a heat sink; b) a heating component in thermal contact with the heat sink; c) a barrier comprising a wall having a top and bottom surfaces, wherein the bottom surface is sealed to the said heating component wherein the sealed barrier and said heating component form a container containing a liquid composition; d) a first piece comprising a plurality of wells, wherein the first piece is sealed to the top surface of the barrier and the wells extend into the container; e) a second piece comprising a plurality of sample vessels, each with an open end, wherein the sample vessels are removably inserted into the wells; f) a third piece comprising a plurality of extrusions, wherein the extrusions are removably inserted into the open ends of the sample vessels. In one embodiment said liquid composition comprises a metal that is liquid above 60° C. and that has a heat transfer coefficient of at least 0.1 W/m*K. In another embodiment said liquid metal is capable of increasing in volume by about 0.1 to 6.0%. In another embodiment said capable of an increase in temperatures is more than 10.5° C./second. In another embodiment said well is adapted to be flexible so that said well is capable of forming a thermal or optical contact with said sample vessels. In another embodiment said adapting comprises utilizing a geometric configuration and/or deformable material in said well. In another embodiment said geometric configuration is polygonal, elliptical or circular. In another embodiment said wells are immersed in said liquid composition to an initial level. In another embodiment said extrusion extends to above, at or below said initial level. In another embodiment said third piece is capable of absorbing heat from or being cooled by said liquid composition. In another embodiment said wells of the first piece are transparent and flexible, and the sample vessels of the second piece are transparent, whereby increased pressure on said wells places said liquid in said container in thermal and optical contact with a sample in said sample vessel. In another embodiment said extrusions of the third piece are transparent. In another embodiment said barrier is sealed to each of a heat spreader and the first piece through a gasket. In another embodiment said first piece or second piece comprises a reflective surface. In another embodiment the barrier is sealed to each of a heat spreader and the first piece with a fastener. In another embodiment said apparatus further comprises a heat spreader in contact with said heating component. In another embodiment said heating component is a Peltier, wire elements or a combination thereof. In another embodiment said apparatus further comprises a second heating component, wherein said barrier is disposed between said heating component and said second heating component. In another embodiment said plurality of wells comprise 4, 8, 16, 32, 48, 96, 196, 384 or 1536 wells. In another embodiment said apparatus further comprises a fan and stir bar, wherein optionally said fan and stir bar are operatively connected to a single motor. In another embodiment said apparatus is powered by a battery. In another embodiment said fan is turned on and off automatically by a controller component operatively connected to said apparatus. In another embodiment said apparatus further comprises a metal heat spreader. In another embodiment said spreader comprises copper. In another embodiment said heating component is configured for gradient PCR.

In another aspect this invention provides a continuous flow PCR system comprising a sample preparation module; thermal cycler, wherein said thermal cycler comprises a liquid composition for modulating temperature in said sample; and an optical assembly for detecting an emission signal from said sample. In one embodiment said system further comprises a sampler and a waste collection.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1A:
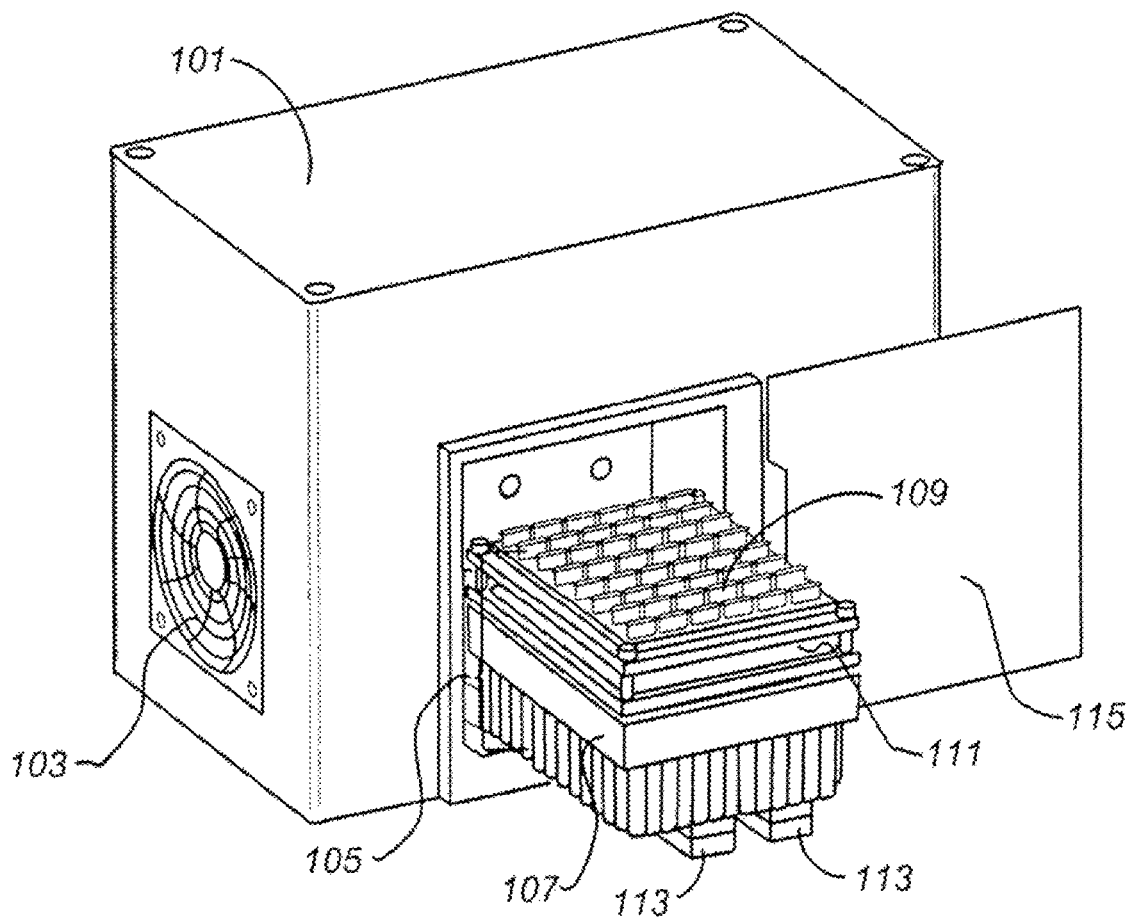
FIG. 1 illustrates a thermal cycler body for use with a liquid composition swap heat block. (A) A 48-well "swap block" device is depicted on sliding rails. The block is slid out, loaded with a sample vessel well plate and sample well plate caps, and then slid into thermal cycler body and the door is closed. The thermal cycler body may comprise an optical assembly, control electronics, fans, and optionally a power supply. (B) Thermal cycler body with "swap block" slid into the operating position.

This invention provides an apparatus comprising a thermal cycler for cycling the temperature of a sample vessel containing a reaction mixture, an optical assembly for detecting signal from the sample vessel and control means for controlling the operation of the thermal cycler and the optical assembly. In certain embodiments the thermal cycler employs a heat block comprising a liquid composition (such as a liquid metal or a thermally conductive fluid) with high thermal conductivity to rapidly cycle the temperatures in the sample vessel. The use of a liquid metal provides two main advantages. First, metal has high thermal conductivity, providing rapid heat transfer. Second, liquid provides tighter contact between the thermally conductive material and the sample vessel, providing more uniform heat transfer. As a result, the temperatures within the sample vessels are remarkably uniform. The combination of rapid temperature ramp rates and uniformity of temperature decreases non-specific hybridization and significantly increases the specificity (e.g., signal-to-noise ratio) of amplification in PCR within individual sample vessels as well as across multiple sample vessels located in the same heat block. In another embodiment, the sample vessel, alone or in combination with the thermal cycler, emits substantially all of a signal generated therein out through a discrete portion of the sample vessel, for example, the top of the vessel, whereby the emitted light can be collected by the optical assembly. In yet another embodiment a light detector detects substantially all of the light emitted from a sample vessel. In certain embodiments the liquid metal or sample vessel is highly reflective and reflects light transmitted through the walls of a transparent sample vessel back into the sample vessel. In this way, a greater proportion of a light signal generated inside the sample vessel is emitted from a discrete portion of the sample vessel, whereby it can be collected by the optical assembly. The ability to collect more light from the reaction means that less expensive optics can be employed in the device, thereby decreasing the cost. Furthermore, collecting light from a discrete location of the vessel eliminates the necessity of removing the vessel from the heat block when performing real time PCR. Thus, the configuration of the heat block allows rapid ramp times and uniform temperatures, and the collection of reflected light from the top of the vessel by the optical assembly without removing the vessels from the heat block, allows real time PCR to proceed more quickly. Accordingly, the apparatus of this invention is particularly adapted for performing PCR (polymerase chain reaction), reverse transcription PCR and real time PCR. Thermal cyclers comprising the liquid metal heat block will perform PCR faster and more cheaply than devices presently available on the market. In one embodiment a thermal cycler comprising a heat block comprising a liquid composition is powered by a battery. In another embodiment a thermal cycler comprising a heat block comprising a liquid composition is powered by a AC or DC current.

In addition to heating blocks for PCR, the liquid metal heating blocks of the present invention can be used widely in the field of biotechnology and chemistry. Examples include but are not limited to incubations of enzymatic reactions such as restriction enzymes, biochemical assays and polymerase reactions; cell culturing and transformation; hybridization; and any treatment requiring precise temperature control. Based on the present disclosure, one of ordinary skill in the art can readily adapt the liquid metal technology to various analyses of biological/chemical samples which require accurate temperature control.

Thermal Cycler

Figure 7:
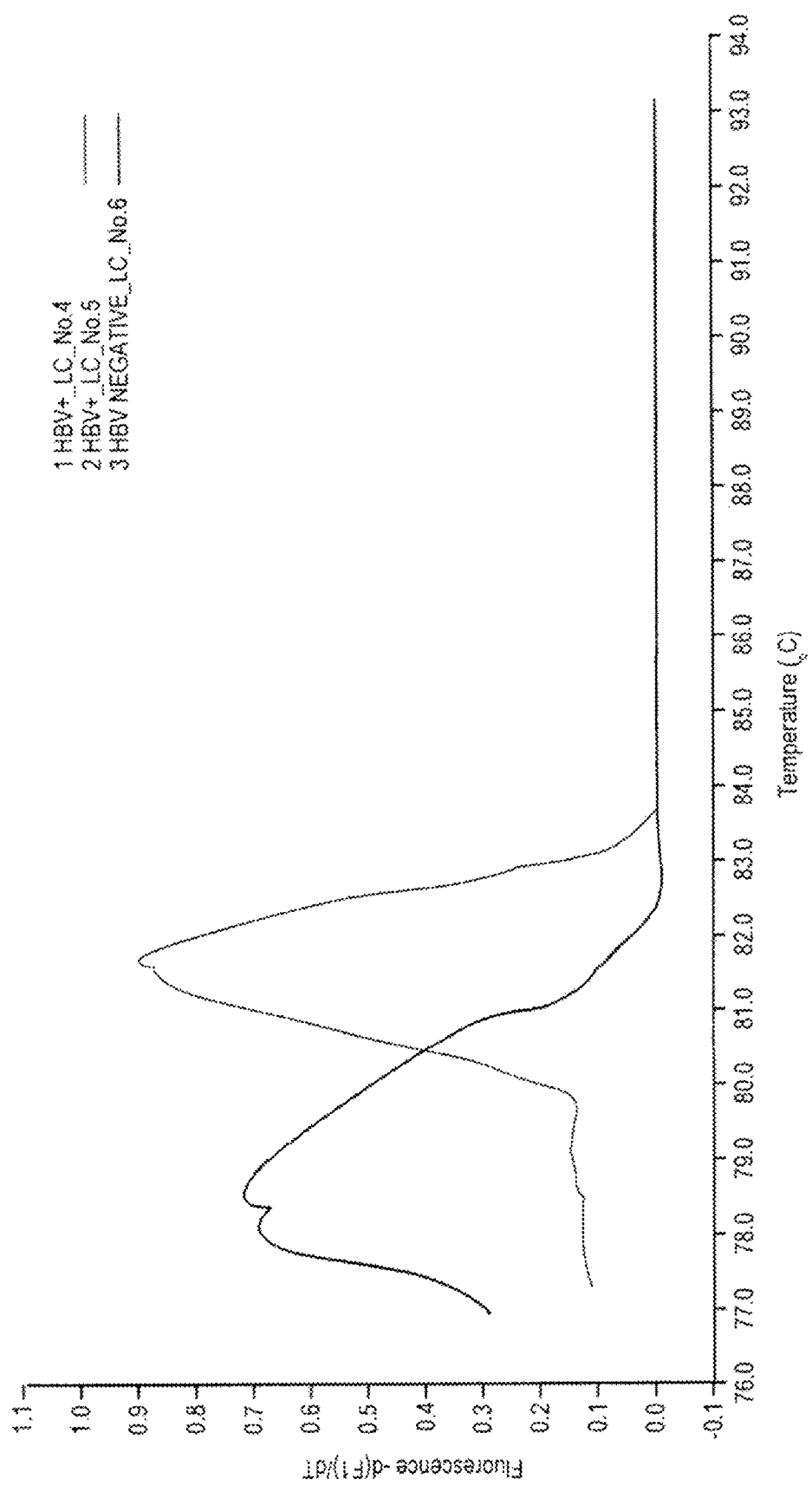
FIG. 7 illustrates PCR amplification using primers specific for the HBV virus and a patients blood sample, wherein the PCR was run on a Roche Lightcycler. The melting curve's positive peak (green) indicates an HBV+ test, but the negative control peak (brown) is also prominent.
Figure 8:
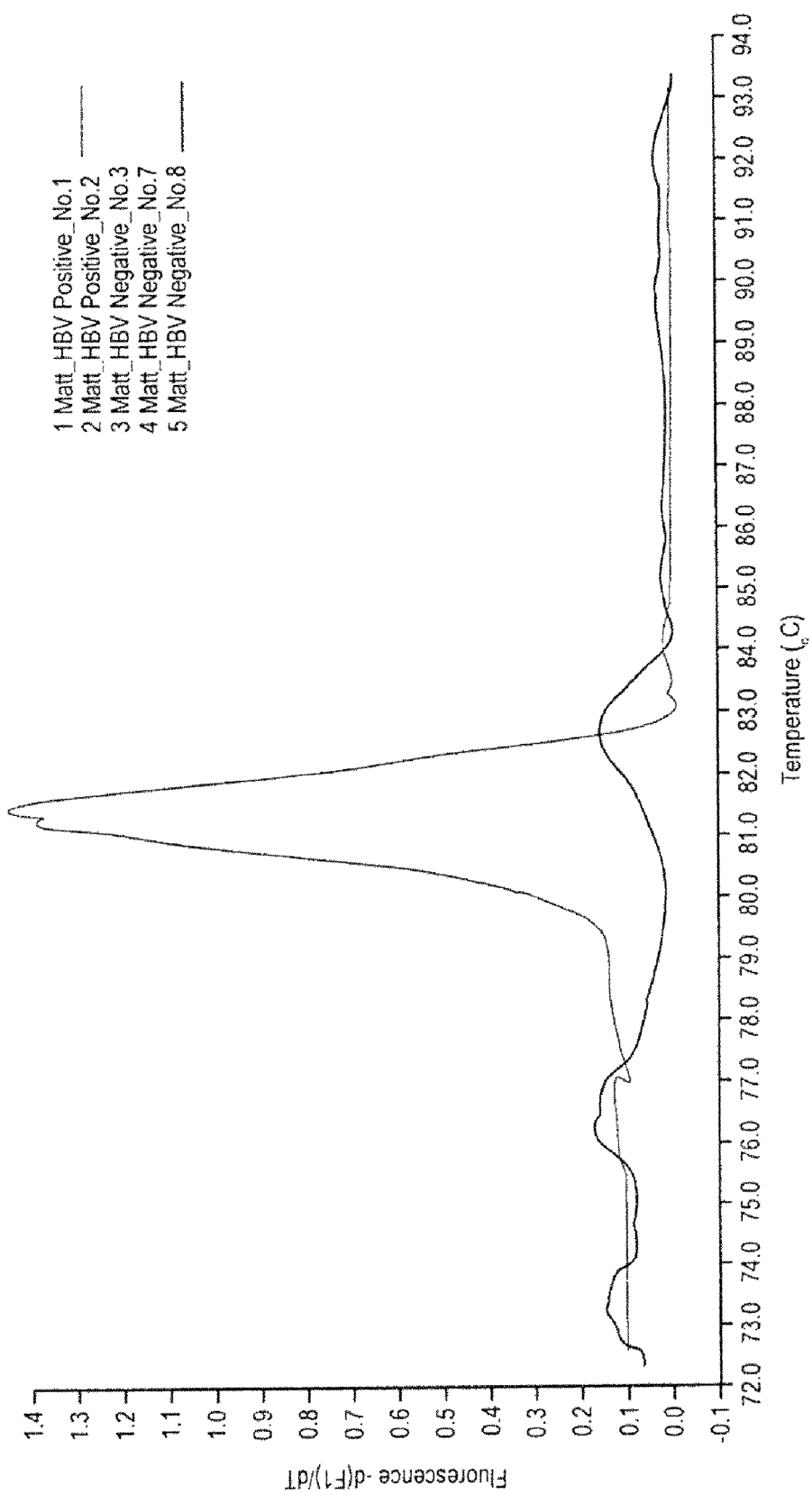
FIG. 8 illustrates PCR amplification using the same primers and sample as that used in FIG. 7, wherein the PCR was carried out using a thermal cycler comprising a liquid metal heat block. The positive peak (green) indicates an HBV+ test, and the negative control peaks (brown, pink) are much less prominent than in FIG. 7. This is indicative of a more accurate HBV+ test result.
Figure 9:
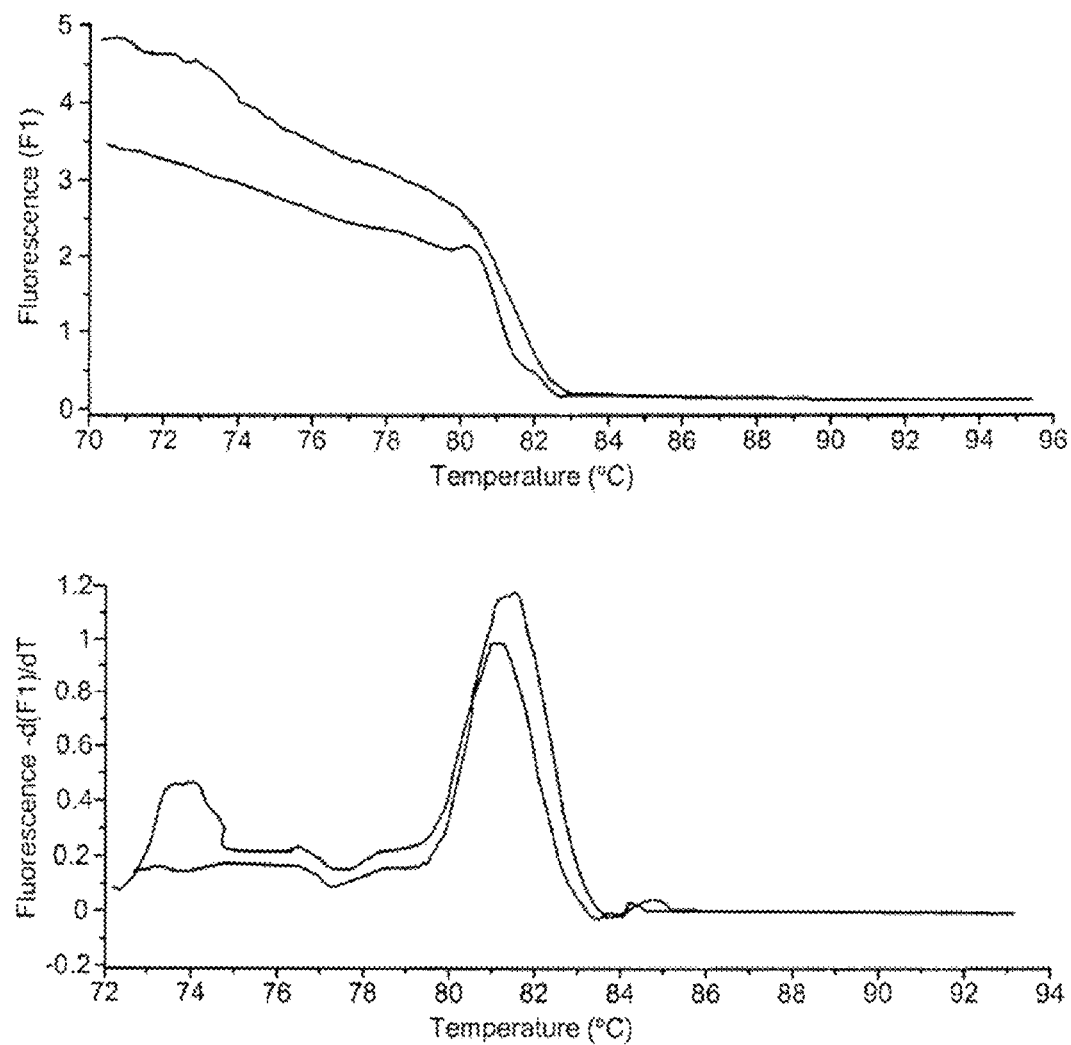
FIG. 9 illustrates results from PCR performed in a thermal cycler comprising a liquid metal heat block in comparison with results from a Roche Lightcycler. Melting curves were run simultaneously with two samples: one in which PCR was performed In a Roche Lightcycler (green) and one in which PCR was performed in our invention (brown). The Roche PCR produced an extra peak, at a temperature indicative of primer-dimer formation, indicating PCR performed in the Roche machine was less accurate than PCR performed in a thermal cycler comprising a liquid metal heat block.

The use of a liquid composition, such as a liquid metal or a thermally conductive fluid, as a heating and cooling medium for a heating block, results in a more uniform heat transfer and more rapid heating and cooling cycles than solid metal heat blocks. In embodiments where a liquid metal heat block is used as a thermal cycler, the faster heat ramping, and superior thermal uniformity lead to lower error rates by DNA polymerases than when used in conventional thermal cyclers (FIGS. 7-9). This is due to the decreased time in which the PCR sample spends at sub-optimal temperatures. Further, the error rates are decreased during long amplifications, SNP identification and sequencing reactions, because of the enhanced thermal uniformity.

In one embodiment a liquid metal or a thermally conductive fluid is used as a heating and cooling medium for a heating block, wherein the heat block comprises at least a base and walls to contain the liquid metal or a thermally conductive fluid. The liquid metal or a thermally conductive fluid provides a more uniform temperature throughout the heat block than conventional heat blocks, because of faster heat transfer within the liquid metal or a thermally conductive fluid and the ability to use convection or stirring to distribute heat.

In another embodiment the heat block comprises a liquid metal or thermally conductive fluid in direct contact with sample vessels. In this embodiment full contact with sample vessels can be achieved, resulting in uniform heat transfer regardless of the type, size, and shape of the sample vessels. Pre-formed wells are not required. Furthermore, uniformity of temperature within the heating block can be achieved, because the liquid metal or thermally conductive fluid can easily be circulated in the heating block by convection or by an external force, including but not limited to a stir bar, a pump, a vibration device, or magnetohydrodynamic (MHD) force.

In yet another embodiment the liquid metal or thermally conductive fluid is completely contained within the heat block and does not contact the sample vessels. In this embodiment the container has receptacles which are designed to accept sample vessels of a desired shape and size. These receptacles are designed to closely fit the sample vessels placed in the wells. In one embodiment these receptacles are made out of a substantially transparent material that allows light transmitted into them to be reflected back into the sample vessel from the liquid metal. In an alternative embodiment the receptacles are made out of a reflective material that reflects substantially all of the light to enter or that is created in a sample vessel in a receptacle well back into said sample vessel. In another embodiment the receptacle may be made out of an opaque material that is neither transparent nor substantially reflective.

In one embodiment the receptacle is manufactured from a flexible material, so that the wells of the receptacle conform to fit tightly with the sample vessels. The tightness of the contact between the wells of the receptacle and the sample vessels increases as the heat block increases in temperature and the liquid metal or thermally conductive fluid expands in volume. The receptacles may be manufactured from an opaque, transparent, semi-transparent or translucent material.

In either the open or closed embodiment the heat block may optionally include a reservoir of liquid metal or thermally conductive fluid which may be part of the heat block, such as depression or bulge in bottom or sidewall of the heat block, or as a separate reservoir connected to the heat block by a connector, such as a tube. This reservoir can optionally be connected by a pump to the heat block. Depending on its design the reservoir can serve as an overflow to capture any liquid metal or thermally conductive fluid as it expands beyond the volumetric limits of the heat block, to maintain or alter internal pressure in a sealed or closed heat block, or as a reservoir for liquid metal lost during use.

In one embodiment the reservoir is used to replenish the liquid metal or a thermally conductive fluid during operation of the heat block. A reservoir containing additional liquid metal or a thermally conductive fluid may be provided to replenish losses as they occur. The replenishment system may keep the liquid metal at a desired level, or in closed embodiments keep the liquid metal or a thermally conductive fluid at a desired pressure. In one embodiment a detection system is provided that electrically monitors the level of liquid metal or a thermally conductive fluid and warns the operator when it is low. This replenishment system may take any convenient form such as a side or bottom secondary reservoir fitted with a plunger or pump to displace liquid metal or a thermally conductive fluid, a control to operate the plunger or pump, and a sensor. For example the sensor may comprise a wire positioned at a defined height which completes a circuit with the liquid metal when the liquid metal is at a desired height. In another embodiment the sensor may comprise an optical beam such that the optical beam shines horizontally at the top of the cavity containing the liquid metal and illuminates the sensor if the liquid level is too low. In another embodiment the sensor comprises two optical beams, one above the other, the lower one indicating a low level and the upper one a high level. A signal can be relayed to the operator or to a control device that would indicate the level of the liquid metal or a thermally conductive fluid. The signal can either indicate to an operator that corrective action should be taken (by raising or lowering the level of liquid metal or a thermally conductive fluid). In another embodiment the control system automatically adjusts the level of the liquid metal or a thermally conductive fluid to reach a desired level. In yet another embodiment the liquid metal or a thermally conductive fluid heat block comprises a user accessible chamber that the user can replenish with liquid metal or a thermally conductive fluid as needed. In one embodiment, the user accessible chamber connects with the liquid metal or a thermally conductive fluid heat block chamber at the bottom and can be filled from the top.

Swap Block

Figure 1B:
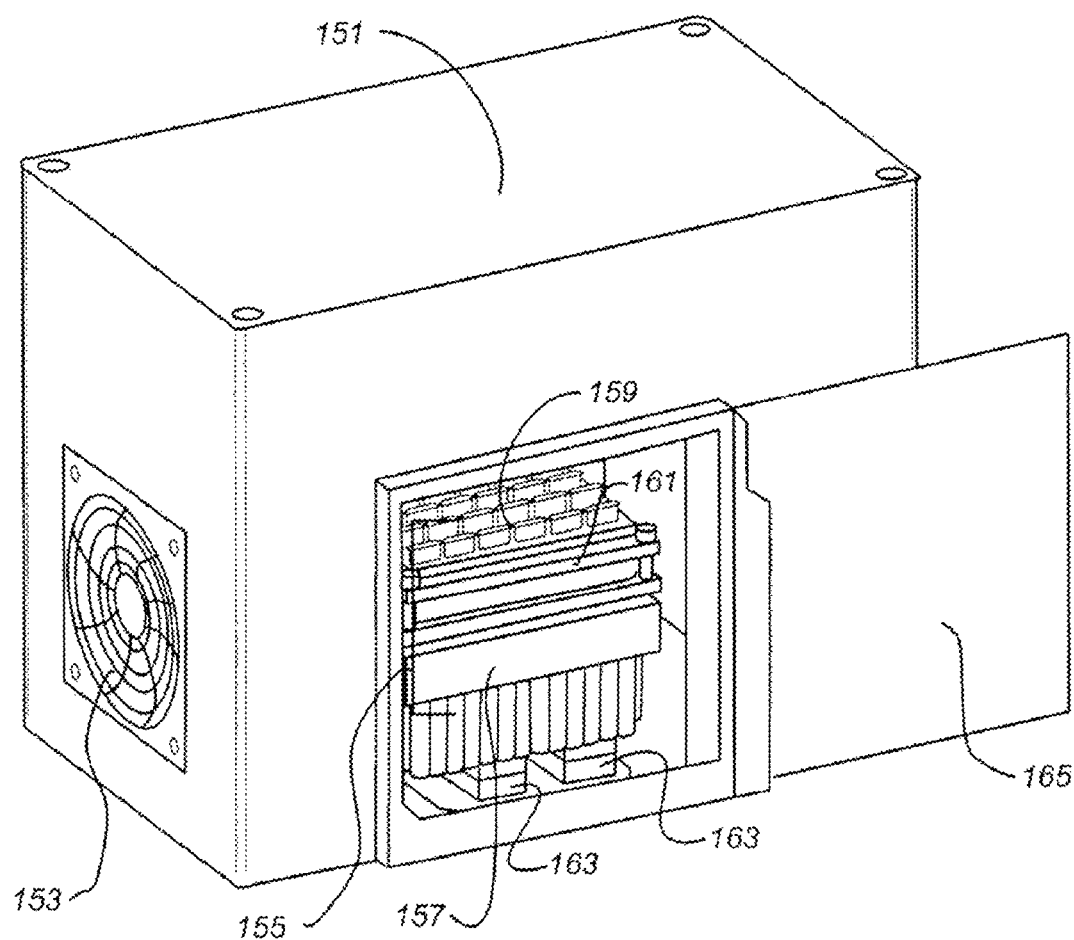
Figure 2:
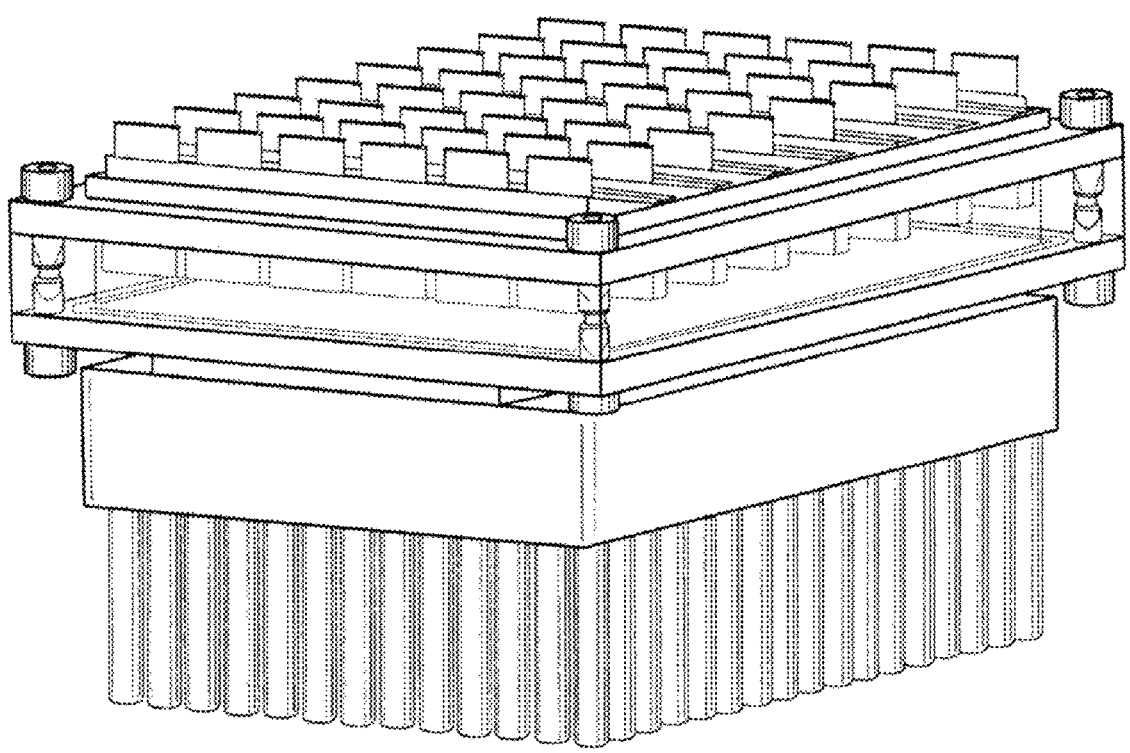
FIG. 2 illustrates a swap block embodiment comprising 48 sample vessel wells. In this embodiment the swap block comprises, from top to bottom: a single piece serving as 48 transparent caps; a single piece creating 48 sample vessel wells; a single receptacle piece with 48 reaction well, which forms the ceiling of liquid metal container; a plastic housing forming walls of liquid metal container; a metal plate forming bottom floor of liquid metal container; a Peltier device(s) for heating and cooling; and a metal heat sink for removing heat from Peltier device(s).
Figure 3:
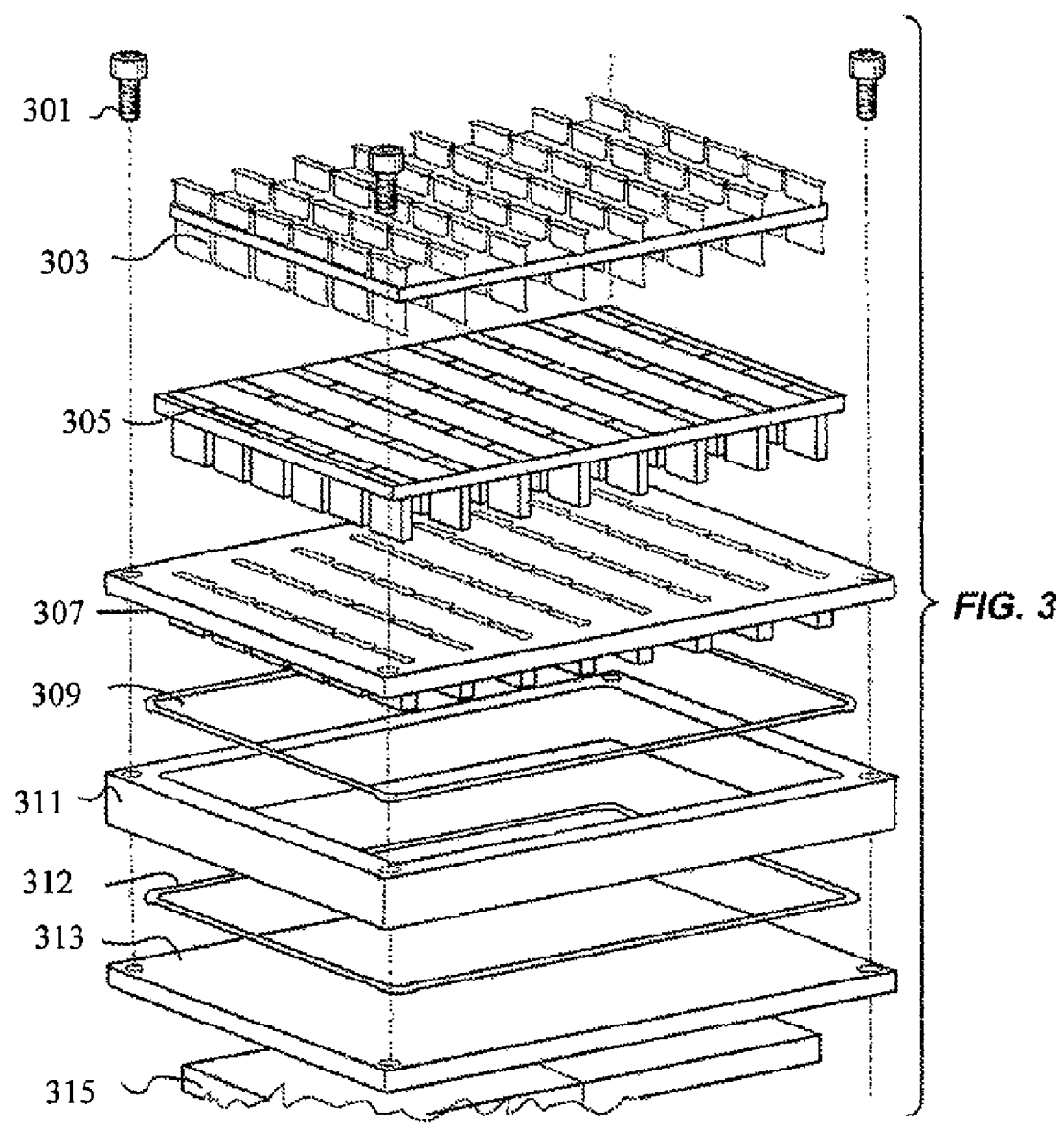
FIG. 3 illustrates an exploded view of a swap block embodiment. In this embodiment the swap block comprises, from top to bottom: a single piece serving as 48 transparent lids. a single piece serving as 48 transparent caps; a single piece creating 48 sample vessel wells; a single receptacle piece with 48 reaction well; a rubber or plastic gasket or ring that forms a liquid tight seal to contain the liquid metal; a plastic housing forming walls of liquid metal container; a rubber or plastic gasket or ring that forms a liquid tight seal to contain the liquid metal; and optionally a metal plate forming bottom floor of liquid metal chamber; a Peltier device(s) for heating and cooling; and a metal heat sink for removing heat from Peltier device(s).
Figure 4:
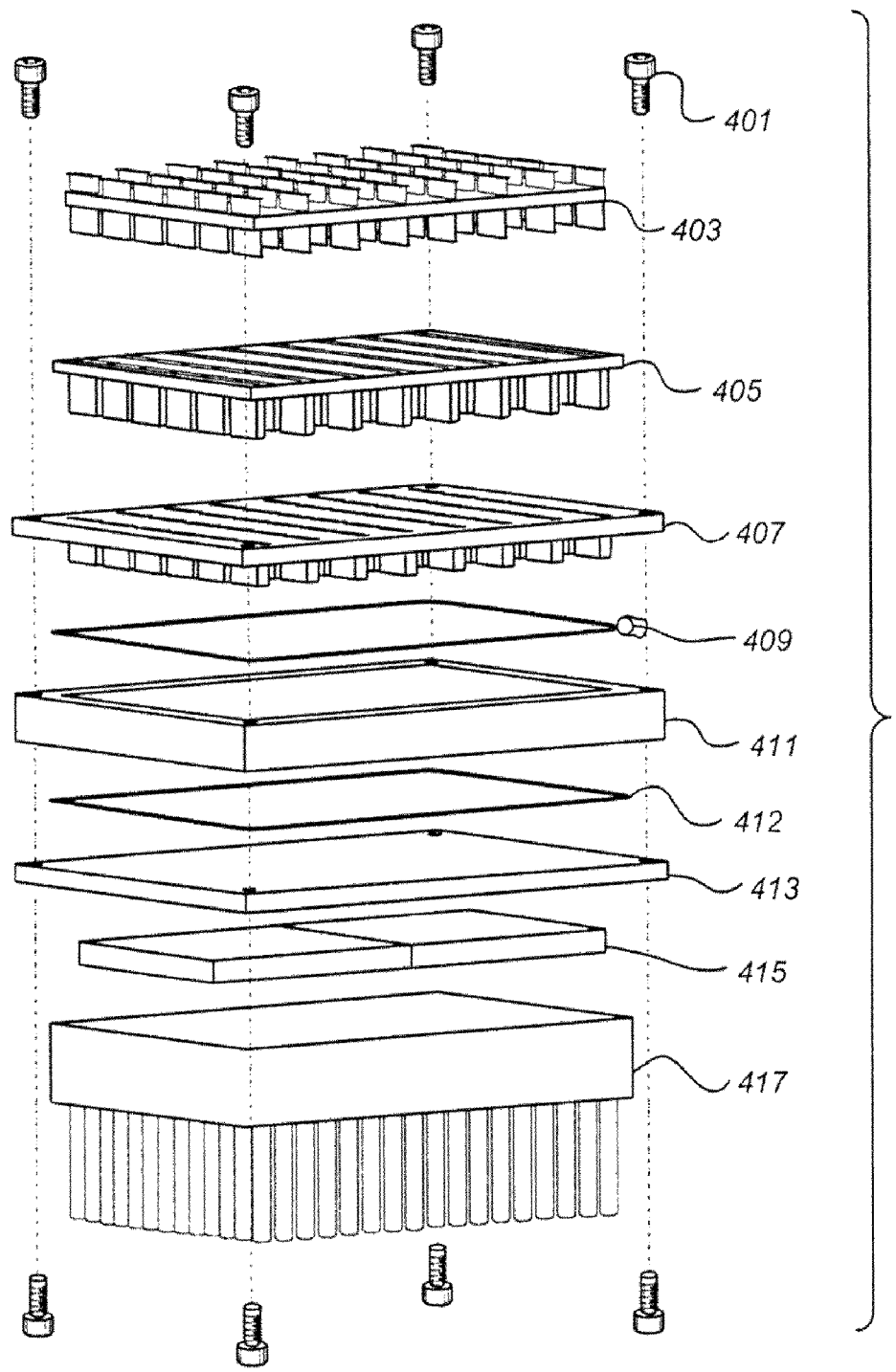
FIG. 4 illustrates a second view of a swap block embodiment. In this embodiment the swap block comprises, from top to bottom: a single piece serving as 48 transparent caps; a single piece creating 48 sample vessel wells; a single receptacle piece with 48 reaction well; a rubber or plastic gasket or ring that forms a liquid tight seal to contain the liquid metal; a plastic housing forming walls of liquid metal container; a rubber or plastic gasket or ring that forms a liquid tight seal to contain the liquid metal; a metal plate forming bottom floor of liquid metal chamber; a Peltier device(s) for heating and cooling; and a metal heat sink for removing heat from Peltier device(s).

In one embodiment, a thermal cycler body (101; 151) comprises a fan (103; 153) and a removable heat block assembly, or swap block (105; 155) (FIG. 1). The swap block (105; 155) is inserted into and removed from the thermal cycler body (103; 153) by optionally sliding the swap heat block on sliding rails (113;163). After the swap block (105; 155) is inserted into the thermal cycler body (103; 153) the door of the thermal cycler (115;165) may be closed. The swap heat block (105; 155) comprises a liquid composition container (111; 161) and a heat sink (107;157) and optionally capped samples (109;159). In one embodiment the swap heat block (FIG. 2) comprises a receptacle with wells that seals the in the liquid composition so that the sample vessels do not contact the liquid (metal, metal alloy or metal slurry). In another embodiment the swap block (105; 155) comprises a receptacle barrier with wells (307;407) that is sealed to a liquid composition container housing (311;411), wherein the seal is liquid tight and may optionally comprise a gasket (309;409) (FIGS. 3 and 4). Further, the liquid composition container housing (311;411) is sealed to a base plate (313;413), which may be a metal plate (such as copper or aluminum), wherein the seal is liquid tight and may optionally comprise a gasket (312;412). The base plate (313;413) is in turn thermally coupled to a Peltier element (315;415), heats and cools the liquid composition and is in turn coupled to a heat sink (417). Optionally, a heat spreader (such as a copper, aluminum, or other metal or metal alloy that has high thermal conductivity) is sandwiched between the base plate (313;413) and the Peltier element (315;415). In some embodiments the swap block (105; 155) is held together by fasteners, such as screws (301;401). In one embodiment the swap block comprises a first piece, such as a receptacle with 48 wells (307;407), that is occupied by a second piece, such as a sample vessel, including but not limited to a sample plate (305;405), a single sample vessel or a strip of sample vessels, into which a third piece, such as a transparent cap plate (303;403), a single cap or strip of caps is inserted. In one embodiment the transparent cap plate (303;403), a single cap or strip of caps optionally comprises an extrusion, such as a light guide.

In another embodiment, the sample vessels are placed directly into the liquid. In yet another embodiment, the receptacles provide a ring (e.g., O ring) that functions as a squeegee to wipe clean a sample vessel being removed from the liquid and optionally closes to seal the liquid metal in. In another embodiment, the receptacle provides a sleeve into which the sample vessel is placed (e.g., sleeve composed of a pliable plastic film); in other words, the sleeve functions as a barrier between the sample vessel and the liquid metal or thermally conductive fluid.

Liquid composition (such as liquid metal or thermally conductive fluids) heating blocks maintain a uniform temperature throughout the block. In one embodiment this is achieved through passive forces such as convection currents or passive conduction in a liquid metal or thermally conductive fluid. In an alternative embodiment temperature uniformity is enhanced by actively mixing the liquid metal or thermally conductive fluid using a method such as a stir bar, or a circulation system using a pump or an MHD force.

In one embodiment a pump is used to circulate the liquid metal or thermally conductive fluid in the heat block. Any pump design which can displace the liquid metal or thermally conductive fluid is suitable, such as a positive displacement pump (including but not limited to a rotary-type pump, reciprocating-type pump, roots type pump, a syringe pump, a Wendelkolben pump or a helical twisted roots pump) a centrifugal pump, an MHD pump, or a kinetic pump. In this embodiment the pump will be manufactured out of materials capable of withstanding the temperature differentials and/or corrosive issues associated with liquid metal or thermally conductive fluids.

In another embodiment, a pump is utilized to circulate the liquid and/or to cause the liquid metal or thermally conductive fluid (e.g., increased pressure in the reservoir chamber) to press against the receptacle walls or sample walls depending on the configuration of the thermal cycler (e.g., open versus closed). For example, in a closed system, the increased pressure causes the liquid to exert pressure against the receptacle walls, thus causing such walls to press closely against the sample vessel walls, forming a junction. Such junction enhances thermal conductivity and/or optical transmittance. In embodiments where an open system is used (e.g. the sample vessels are in direct contact with a liquid composition) the pump may increase the level of the liquid metal or thermally conductive fluid such that it contacts a greater surface areas of the receptacle walls.

In another aspect of the invention, where samples are placed directly into the liquid (metal, metal alloy or metal slurry), such sample vessels would naturally be subject to buoyant force equal to the displacement of liquid. In various embodiments, a clip, lid, fastener, weight, spring clasp, screw plate, or such means is utilized to ensure the sample vessels are firmly kept in place.

In an alternative embodiment a MHD force is used to circulate the liquid metal. The liquid metal is exposed to a magnetic field formed in one direction and an electrical field formed in a direction perpendicular to the direction of the magnetic field. The liquid metal then flows in a direction perpendicular to both the direction of the magnetic field and the direction of the electrical field. By using both a magnetic field and an electrical field, it is possible to cause liquid metal to flow in a designated direction without physical control such as control by a pump. These field characteristics can be used to introduce currents in the heat block in order to maintain a uniform temperature or to introduce and discharge liquid metal into and from the heating block, for example to a reservoir. In a related embodiment the electrical field is formed by DC or AC current, as the frequency is modulated, the flow of the liquid metal oscillates in relation to the change in frequency, thereby achieving high uniformity of temperature throughout the heat block.

In another embodiment the liquid metal or thermally conductive fluid may be circulated by a stir bar. The stir bar may be linked to a motor which causes it to stir, or it may be magnetically responsive and stir in response to a change in magnetic field. In one embodiment the stir bar is resistant to rapid changes in temperature or it is coated with a covering that is resistant to rapid changes in temperature. In one embodiment the stir bar is a simple horizontal bar. In an alternative embodiment the stir bar may be fan shaped or have multiple projections (such as 3, 4, 5, 6, 7, 8, 9, 10, 11 or 12) which serve to stir the liquid metal or thermally conductive fluid. In one embodiment the thermal cycler (101) comprises a motor operatively linked to a fan (103) and a stir bar. In another embodiment the fan and stir bar are connected coaxially to the same motor and optionally turn simultaneously.

In yet another embodiment the liquid metal or thermally conductive fluid may be circulated by a vibration device. The vibration device may be integrated into the thermal cycler or heat block structure, or it may be a secondary device in contact with the heat block or thermal cycler. The vibration device will transfer waves of vibration through the liquid metal or thermally conductive fluid, aiding in its convection and decreasing the time it takes for the metal to reach thermal uniformity. In one embodiment an acoustical device is used to vibrate the liquid metal or thermally conductive fluid, such as a piezo mixer, ultrasonic vibrator, subsonic vibrator or other sonic device. The vibrator may comprise speaker coils or piezos or mechanical motors. Vibratory devices also may shake the sample and PCR reagents in the sample vessels thus mixing the contents allowing the reaction to occur more efficiently.

Liquid metals or a thermally conductive fluid are flowable during the operation of a thermal cycler and have a boiling point higher than the operation temperature. Further, the liquid metal or thermally conductive fluid is preferably non-toxic under conditions of operation. Liquid metal has high heat and electrical conductivity and thus can be very responsive to heating and cooling patterns/cycles. For polymerase chain reaction (PCR), rapid heating and cooling rates are preferred, which liquid metals or thermally conductive fluids can satisfy.

Sandwich Heat Block

Figure 5A:
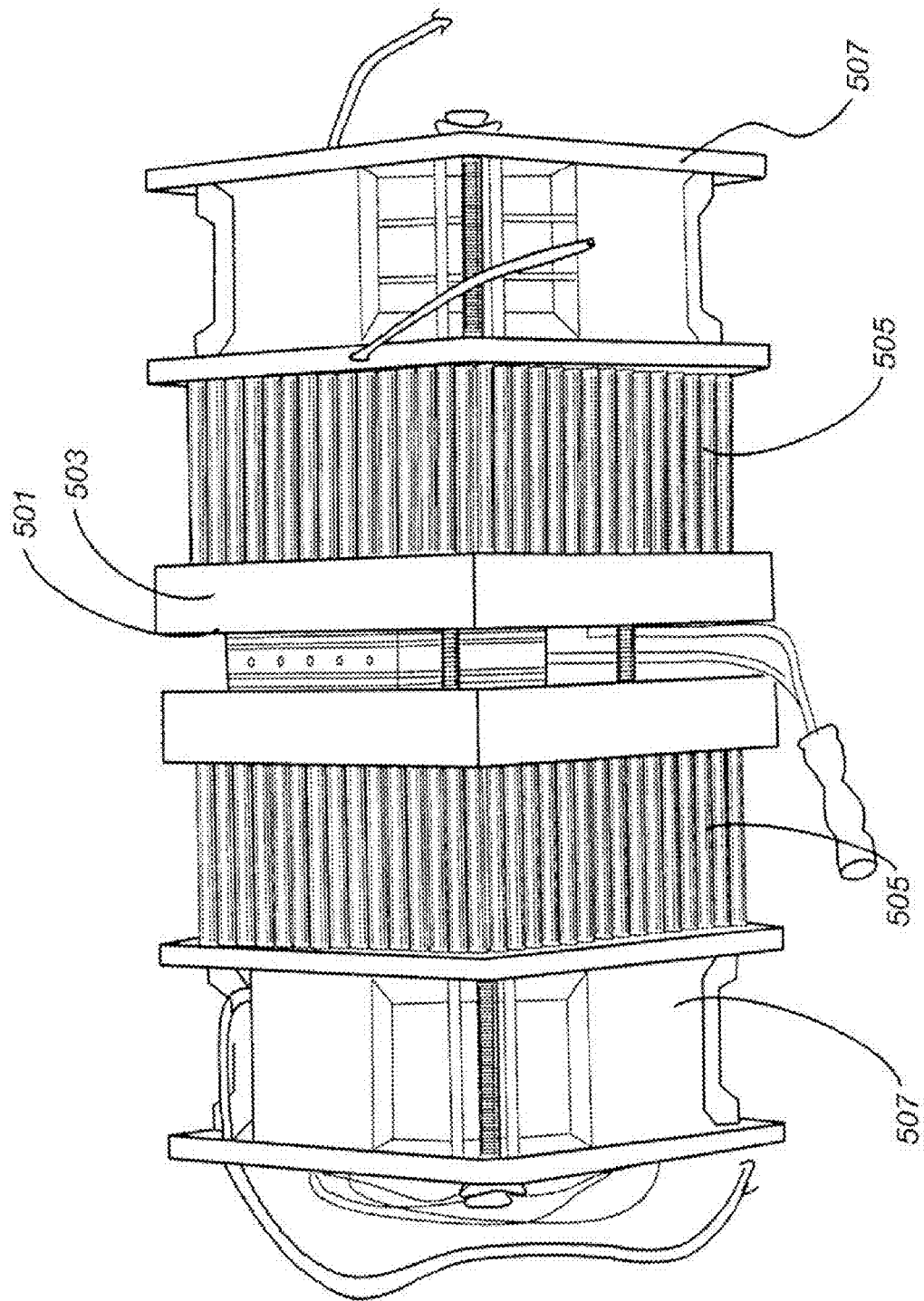
FIG. 5 illustrates a view of a sandwich embodiment of a thermal cycler component comprising a heat block comprising a liquid metal. (A) This view shows a liquid metal chamber is formed between two Peltier devices (two large walls) and the brown plastic piece, built as a square plastic ring (four narrow walls). The liquid metal chamber comprises holes for capillary samples tubes. Further, each Peltier device is thermally coupled to a heat sink, which is in turn connected to a fan. (B) A close up of the central portion of the heat block sandwiched between the Peltier devices. (C) the liquid metal chamber comprises holes for capillary samples tubes. Capillary tubes are slid into holes, and immersed directly in liquid metal composition for thermal cycling. Peltier devices are located on both sides of liquid metal reservoir to allow rapid heating and cooling.
Figure 5B:
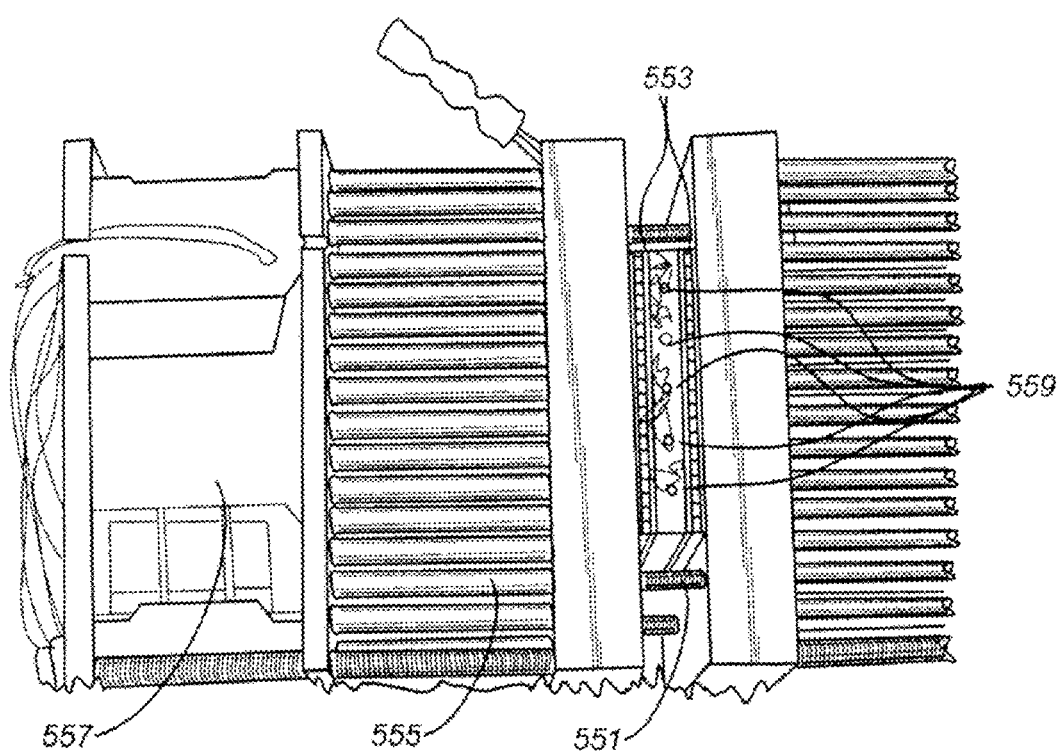
Figure 5C:
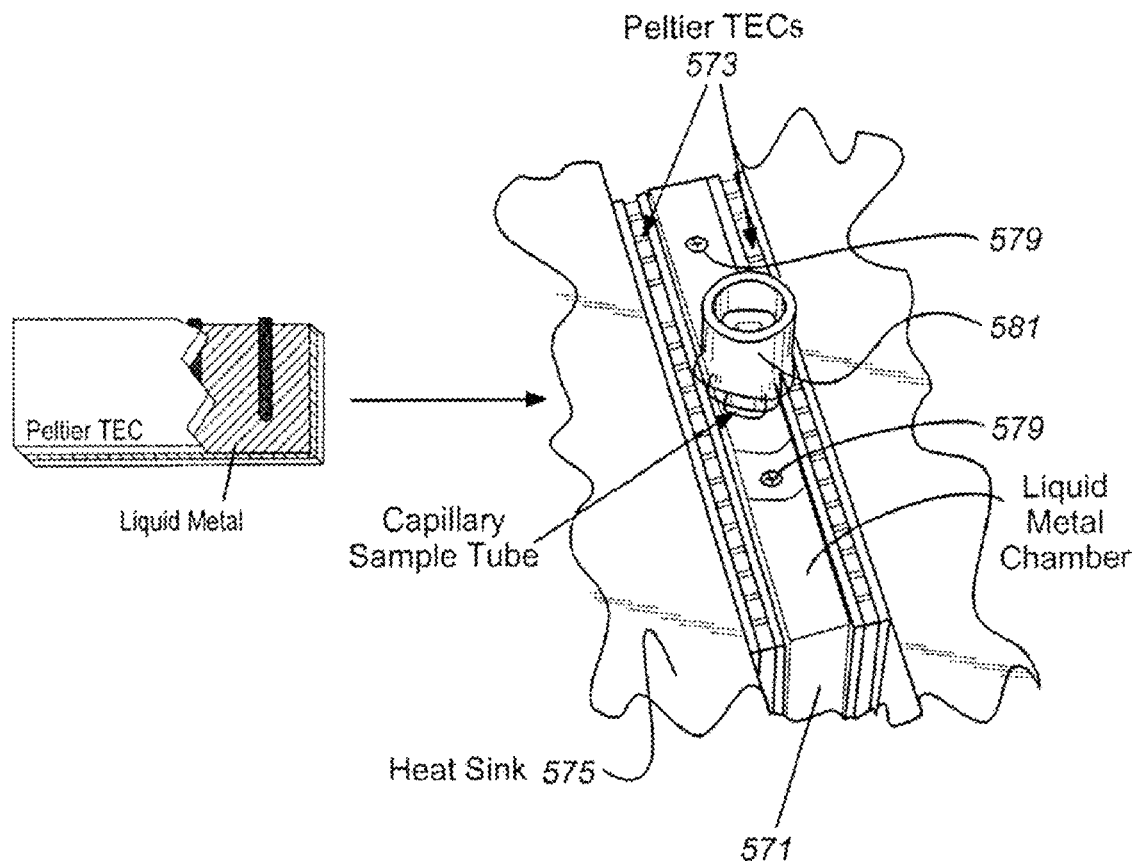

In another aspect of the invention, the thermal cycler comprises a sandwich liquid composition heat block (FIG. 5). In an embodiment the sandwich heat block comprises a liquid composition container (501;551;571) that is thermally coupled to Peltier heating and cooling elements (503;553;573), which is in turn thermally coupled to heat sinks (505;555;575) and optionally coupled to flanking fans (507;557). In this embodiment the liquid composition container (501;551;571) comprises openings for sample vessels (559;579) such as capillary tubes (581). In one embodiment the sample vessels are indirect contact with the liquid composition. In an alternative embodiment, the samples are physically separated from the liquid composition by thermally conductive deformable tube. In one embodiment the heat sink comprises tubes or fins for increasing the radiative surface of the heat sink. In another embodiment the openings for the sample vessels (559;579) comprise a rubber or plastic O-ring which acts to form a seal around the sample vessel placed through the opening into the liquid composition and to squeegee off the liquid composition that may adhere to the sample vessel upon its withdrawal from the heat block. Sandwich heat block embodiments may comprise openings for at least 1 sample vessel, such as 2, 3, 4, 5, 6, 7, 8, 10, 12, 16, 20, 24, 30, 36, 42, 48, 54, 60, 66, 72, 78, 84, 90, 96, 192, or 384 sample vessels.

In another embodiment, holes are provided on both sides so that the tops and bottom of the sample vessels are visible. In such an embodiment, the liquid is encased in the plastic barrier with holes going through the plastic barrier (e.g., multiwell configuration) so that a sample vessel sits in a well. In this configuration a photodiode and optical detector may be arrayed on opposite sides of a given well. This allows realtime or quantitative PCR to be performed by inducing a light signal into one part of the sample vessel (e.g. the top) and detecting any emanating signal from the other side of the block (e.g. the bottom), or vice versa.

In one embodiment, one or more capillary tubes (581) of a thermally conductive plastic, such as that available from Cool Polymers (Inc., 333 Strawberry Field Rd., Warwick, R.I. 02886USA; http://www.coolpolymers.com) is inserted into a heat block comprising a liquid metal (501;551;571). In one embodiment the capillary tube (581) may penetrate through the opposing side of said heat block, providing optical access to both the top and bottom of the tube. In this embodiment a sample within the tube (581) can be excited on one end and any resulting signal can be detected on the other. In one embodiment the tube (581) directly contacts the liquid metal. In an alternative embodiment the tube (581) is inserted into a highly thermally conductive deformable tube (such as a plastic tube) within the liquid metal comprised within the heat block. In this embodiment it is possible to insert a sample vessel into the highly thermally conductive deformable plastic tube. The liquid metal could then be pressurized by using a pump, wherein the pressure squeezes the thermally conductive plastic tube to form a tight contact with the sample vessel.

Continuous Flow Heat Block

In an alternative embodiment the liquid metal or thermally conductive fluid heat block may be used in a continuous PCR thermal cycler. Continuous PCR thermal cyclers can be used when highly sensitive or high throughput PCR is desired. There are many situations in which one might want to sample air, blood, water, or other medium continuously in a sensitive PCR assay. This can be used to look for a variety of biological contaminants including influenza, bacterial pathogens, and any number of viral or bacterial pathogens. Continuous PCR allows PCR to be practiced in an automated manner without the need for human interaction. A continuously sampling PCR system can also serve as an early warning system in HVAC systems of buildings, airplanes, busses, and other vehicles, and can be used in the monitoring of blood, water, and other possibly contaminated sources.

Figure 11:
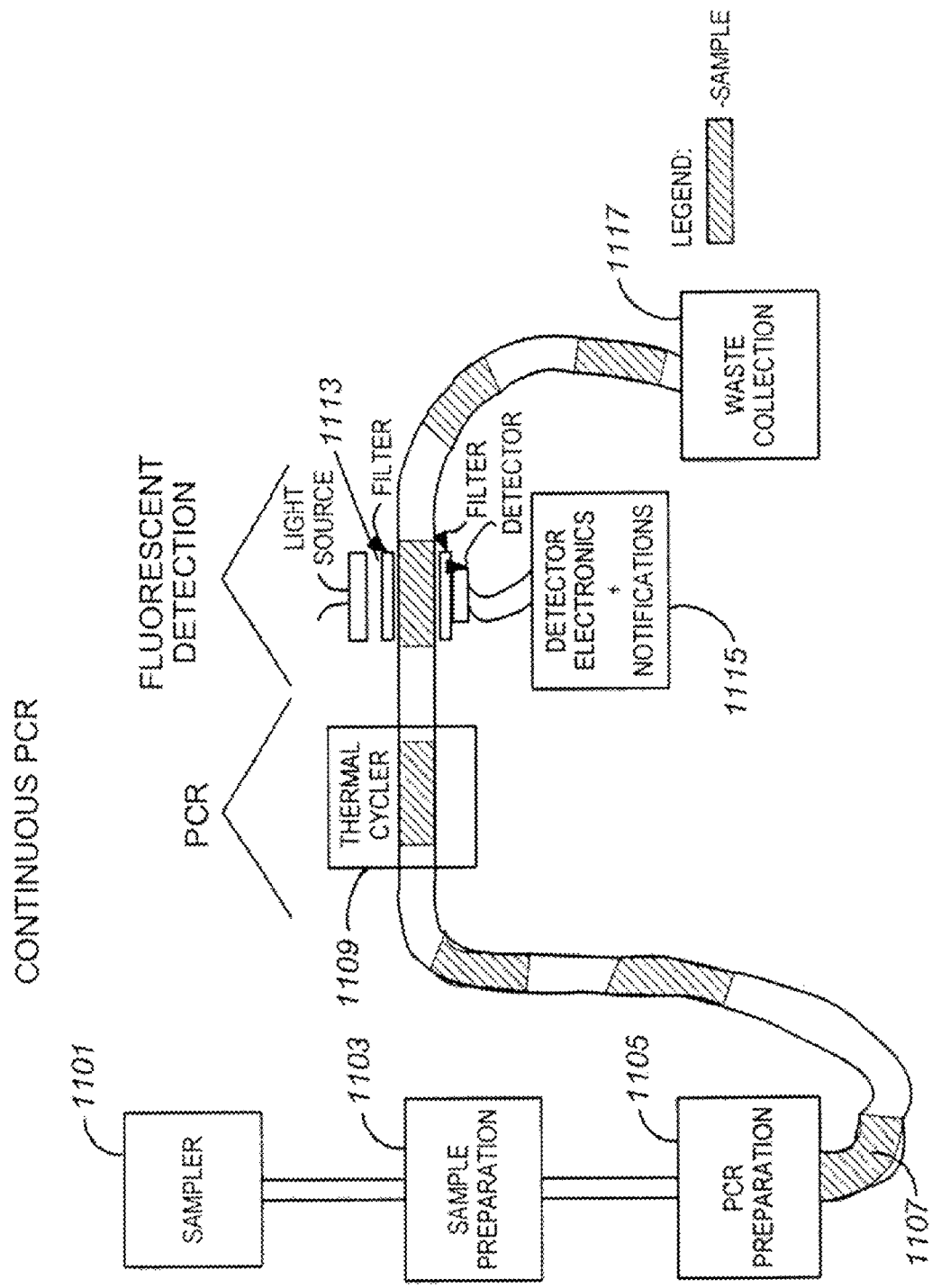
FIG. 11 illustrates the use of a liquid composition heat block for a continuous PCR device. Multiple samples are continuously run through said device to detect one or more specific biological specimens, such as a pathogen or biological contaminant.

In one embodiment the continuous PCR system takes an sample from a collection device, such as an air sampler, fluid sampler or other sampler, (1101) (FIG. 11). In other embodiments condensate fluid collected on the condenser unit of an air conditioning system is used as a starting sample or a specialized gas sampling device that works through direct impaction is used to obtain a sample. The sample is prepared (1103), which in some embodiments may include cell lysis, DNA or RNA purification, filtration, and/or reverse transcription. Then the sample is prepared for PCR (1105) by adding the sample to PCR reagents (such as at least one DNA polymerase, dNTPs, buffer and a salt) and primers, (such as assay-specific primers or broadly applicable primer sets for multiple target pathogens). These primers may be chosen to selectively amplify the DNA or cDNA isolated from a specific pathogen (such as a mold, virus, bacteria, parasite or amoeba), gene, other desired nucleic acid, or any combination thereof.

The PCR sample/reagent cocktail (1107) then flows through a tube to the thermal cycling unit (1109). In some embodiments the tube is a clear or transparent. In another embodiment the tube is opaque. In one embodiment the tube is a cylinder. In another embodiment the tubes cross section comprises one or more planes forming a shape such as a triangle, square, rectangle, pentagon, hexagon, heptagon, octagon, nonagon, decagon, or other polygon. In one embodiment the volume of sample (1107) is such that it takes up a small discrete length of space in the sample vessel, the rest of which is occupied by air, gas, or non-reactive liquid, such as mineral oil. Compressed gas or liquid is used to push the sample into the heat block of the thermal cycler. In one embodiment the heat block is a liquid metal or thermally conductive fluid heat block, which may be heated and cooled by a variety of devices, including but not limited to thermocoupled Peltier thermoelectric module, a conventional thermoelectric module, hot air or hot light. In one embodiment the thermal cycler uses Peltier thermoelectric modules external to the tube to heat and cool the sample as desired.

After the desired number of thermal cycles are complete, the sample is pushed further down the tube using compressed air or liquid, exiting the thermal cycling region and passing into a detection region (1113) in which a fluorescence measurement, absorbance measurement, or other interrogation measurement can be made. In one embodiment the tube is opaque except for the detection region, which is clear or substantially transparent. In the detection region, a light source (such as a coherent light source including but not limited to a laser) is used to excite fluorescent dyes (such as intercalating dyes, including but not limited to ethidium bromide or SYBR green and related dyes) in the PCR sample, and the excitation light is sensed with a photodetector (such as a CCD, CMOS, or other optical detector). The detection electronics (1115) evaluate the signal sent from the detection region (1113) A positive PCR test will yield larger amounts of detected fluorescence than will a negative PCR test.

Next the sample is pushed further down the tube, eventually to be collected as waste in the waste collector (1117). In one embodiment the tube is used for a single use only, then disposed of. In an alternative embodiment the tube can be used to amplify and detect the presence or absence of amplification products in multiple samples. The samples are loaded at intervals and interspaced with a barrier of gas or liquid to prevent intermixing. The samples are spaced apart in the transport tube, allowing each one to be individually cycled and detected. In one embodiment the samples are spaced apart in a manner so that as one is undergoing thermal cycling another sample is in the detection region undergoing interrogation. In another embodiment multiple tubes may be used in parallel to increase sample throughput. In yet another embodiment the system may alert the user when amplification has occurred (a positive result), indicating that the target sequence is present.

Gradient Heat Block

In an alternative embodiment the liquid metal or thermally conductive fluid heat block is designed so that it can maintain different temperatures in different zones of the heat block. This allows different sample vessels located in wells in different zones to be cycled at different temperatures simultaneously, such as during gradient PCR. In one embodiment the liquid metal or thermally conductive fluid heat block is a capable of maintaining a temperature gradient across 2 or more zones, such as 3, 4, 5, 6, 7, 8, 9, 10, 11, 12, 13, 14, 15, 16, 17, 18, 19, 20, 21, 22, 23, or 24 zones. In an embodiment the heat block comprises a receptacle with 1 or more sample vessel wells in each temperature zone, such as 2, 3, 4, 5, 6, 7, 8, 9, 10, 11, 12, 13, 14, 15, 16, 17, 18, 19, 20, 21, 22, 23, or 24 wells. In one embodiment temperature gradients in excess of 0.1° C. to 20° C. across the liquid metal or thermally conductive fluid heat block can be achieved.

In one embodiment the temperature gradient changes in a linear fashion across a single dimension (horizontally or vertically) of the liquid metal or thermally conductive fluid heat block. For example in a heat block comprising a receptacle with 48 wells (307;407) there are 8 rows of 6 wells equally spaced across the block. If a temperature gradient of 8° C. is formed horizontally across the top of the heat block, each row of sample wells will differ in temperature by approximately 1° C.

In some embodiments the heat block will contain internal baffles or insulated walls which act to separate different zones of the liquid metal or thermally conductive fluid from other zones. Each zone may further comprise an individual heat mixer (such as a pump, stir bar or MHD) or the entire heat block may be attached to a single heat mixer such as a MHD or vibration device. Further each zone of the heat block may comprise individual heating and/or cooling elements such as a heat conduction element (wires, tubes), thin foil type heater, Peltier elements or cooling units.

In an alternative embodiment the heat block may comprise multiple heating and cooling devices, some of which act globally across all of the liquid metal or thermally conductive fluid heat zones, and some of which act only within a single zone. For example the heat block may employ uniform heating across the entire length and width of block with additional heating and/or cooling devices adjacent to each zone in the heat block Such an arrangement may provide greater precision for precisely tuning the temperature of the liquid metal or thermally conductive fluid in each zone and the reaction temperature of the associated sample vessels within said zone.

Thermal Conductivity

The liquid composition heat block, containing a liquid metal or thermally conductive fluid, maintains a more uniform temperature across the block in comparison to solid metal heat blocks. Solid heating blocks show a significant variation in temperature both across the block and in sample to sample variation (Schoder et al., J. Clin. Micro Biol. 2005, 43 2724-2728). The variability of temperature at any given point in the heating apparatus is greater for the conventional solid metal thermal cycler than for the liquid metal or thermally conductive fluid heat block. Variability as high as +/−3.3° C. has been observed with conventional thermal cyclers while the greatest variability with the liquid metal or thermally conductive fluid heat block is much lower. In one embodiment the heat block comprises a liquid metal with a heat transfer coefficient greater than 0.1 watts/meter-kelvin (W/m*K), such as between 0.25-85 W/m*K, including but not limited to 0.25 W/m*K, 0.5 W/m*K, 0.75 W/m*K, 1 W/m*K, 1.5 W/m*K, 2 W/m*K, 2.5 W/m*K, 3 W/m*K, 3.5 W/m*K, 4 W/m*K, 4.5 W/m*K, 5 W/m*K, 5.5 W/m*K, 6 W/m*K, 6.5 W/m*K, 7 W/m*K, 7.5 W/m*K, 8 W/m*K, 8.5 W/m*K, 9 W/m*K, 9.5 W/m*K, 10 W/m*K, 11 W/m*K, 12 W/m*K, 13 W/m*K, 14 W/m*K, 15 W/m*K, 16 W/m*K, 17 W/m*K, 18 W/m*K, 19 W/m*K, 20 W/m*K, 21 W/m*K, 22 W/m*K, 23 W/m*K, 24 W/m*K, 25 W/m*K, 26 W/m*K, 27 W/m*K, 28 W/m*K, 29 W/m*K, 30 W/m*K, 32 W/m*K, 35 W/m*K, 37 W/m*K, 40 W/m*K, 42 W/m*K, 45 W/m*K, 47 W/m*K, 50 W/m*K, 55 W/m*K, 60 W/m*K, 65 W/m*K, 70 W/m*K, 75 W/m*K, 80 W/m*K, 85 W/m*K.

In one embodiment the liquid metal or thermally conductive fluid heat block is a component of a thermal cycler which has substantial thermal uniformity across the entire heat block, wherein the temperature between any two sample vessels in the heat block has a variance of no more than +/−0.6° C., such as no more than +/−0.59° C., +/−, 0.58° C., +/−0.57° C., +/−0.56° C., +/−0.55° C., +/−0.54° C., +/−0.53° C., +/−0.52° C., +/−0.51° C., +/−0.5° C., +/−0.49° C., +/−, 0.48° C., +/−0.47° C., +/−0.46° C., +/−0.45° C., +/−0.44° C., +/−0.43° C., +/−0.42° C., +/−0.41° C., +/−0.4° C., +/−0.39° C., +/−0.38° C., +/−0.37° C., +/−0.36° C., +/−0.35° C., +/−0.34° C., +/−0.32° C., +/−0.31° C., +/−0.3° C., +/−0.29° C., +/−0.28° C., +/−0.27° C., +/−0.26° C., +/−0.25° C., +/−0.24° C., +/−0.23° C., +/−0.22° C., +/−0.21° C., +/−0.2° C., +/−0.19° C., +/−0.18° C., +/−0.17° C., +/−0.16° C., +/−0.15° C., 0.14° C., +/−0.13° C., +/−0.12° C., +/−0.11° C., +/−0.1° C., +/−0.09° C., +/−0.08° C., +/−0.07° C., +/−0.06° C., +/−0.05° C., +/−0.04° C., +/−0.03° C., +/−0.02° C., +/−0.01° C., +/−0.009° C., +/−0.008° C., +/−0.007° C., +/−0.006° C., +/−0.005° C., +/−0.004° C., +/−0.003° C., +/−0.002° C., or +/−0.001° C. In another embodiment the liquid metal or thermally conductive fluid heat block has a substantially uniform temperature between any two wells in the heat block receptacle with a variance from a desired temperature of no more than +/−0.6° C., such as no more than +/−0.59° C., +/−, 0.58° C., +/−0.57° C., +/−0.56° C., +/−0.55° C., +/−0.54° C., +/−0.53° C., +/−0.52° C., +/−0.51° C., +/−0.5° C., +/−0.49° C., +/−, 0.48° C., +/−0.47° C., +/−0.46° C., +/−0.45° C., +/−0.44° C., +/−0.43° C., +/−0.42° C., +/−0.41° C., +/−0.4° C., +/−0.39° C., +/−0.38° C., +/−0.37° C., +/−0.36° C., +/−0.35° C., +/−0.34° C., +/−0.32° C., +/−0.31° C., +/−0.3° C., +/−0.29° C., +/−0.28° C., +/−0.27° C., +/−0.26° C., +/−0.25° C., +/−0.24° C., +/−0.23° C., +/−0.22° C., +/−0.21° C., +/−0.2° C., +/−0.19° C., +/−0.18° C., +/−0.17° C., +/−0.16° C., +/−0.15° C., 0.14° C., +/−0.13° C., +/−0.12° C., +/−0.11° C., +/−0.1° C., +/−0.09° C., +/−0.08° C., +/−0.07° C., +/−0.06° C., +/−0.05° C., +/−0.04° C., +/−0.03° C., +/−0.02° C., +/−0.01° C., +/−0.009° C., +/−0.008° C., +/−0.007° C., +/−0.006° C., +/−0.005° C., +/−0.004° C., +/−0.003° C., +/−0.002° C., or +/−0.001° C. In yet another embodiment a sample vessel in the liquid metal or thermally conductive fluid heat block has a uniform temperature within the sample vessel with a variance from a desired temperature of no more than +/−0.6° C., such as no more than +/−0.59° C., +/−, 0.58° C., +/−0.57° C., +/−0.56° C., +/−0.55° C., +/−0.54° C., +/−0.53° C., +/−0.52° C., +/−0.51° C., +/−0.5° C., +/−0.49° C., +/−, 0.48° C., +/−0.47° C., +/−0.46° C., +/−0.45° C., +/−0.44° C., +/−0.43° C., +/−0.42° C., +/−0.41° C., +/−0.4° C., +/−0.39° C., +/−0.38° C., +/−0.37° C., +/−0.36° C., +/−0.35° C., +/−0.34° C., +/−0.32° C., +/−0.31° C., +/−0.3° C., +/−0.29° C., +/−0.28° C., +/−0.27° C., +/−0.26° C., +/−0.25° C., +/−0.24° C., +/−0.23° C., +/−0.22° C., +/−0.21° C., +/−0.2° C., +/−0.19° C., +/−0.18° C., +/−0.17° C., +/−0.16° C., +/−0.15° C., 0.14° C., +/−0.13° C., +/−0.12° C., +/−0.11° C., +/−0.1° C., +/−0.09° C., +/−0.08° C., +/−0.07° C., +/−0.06° C., +/−0.05° C., +/−0.04° C., +/−0.03° C., +/−0.02° C., +/−0.01° C., +/−0.009° C., +/−0.008° C., +/−0.007° C., +/−0.006° C., +/−0.005° C., +/−0.004° C., +/−0.003° C., +/−0.002° C., or +/−0.001° C.

In some embodiments the uniformity of temperature of the liquid metal or thermally conductive fluid heat block is regulated by circulating the liquid metal or thermally conductive fluid in the block. Circulation of the liquid metal or thermally conductive fluid can be created by natural convection or forced convection, such as by the intervention of a device including but not limited to a stir bar, a pump or MHD power, vibration by physical force or MHD power with DC or AC current, etc.

In some embodiments the liquid metal or thermally conductive fluid heat block has a ramp rate or can change temperature at a rate substantially faster than conventional metal heat blocks, such as at a rate of at least 5-50.5° C. per second, including but not limited to a range of at least 10-40° C. per second, more specifically at a rate of at least 5° C., 5.5° C., 6° C., 6.5° C., 7° C., 7.5° C., 8° C., 8.5° C., 9° C., 9.5° C., 10° C., 10.5° C., 11° C., 11.5° C., 12° C., 12.5° C., 13° C., 13.5° C., 14° C., 14.5° C., 15° C., 15.5° C., 16° C., 16.5° C., 17° C., 17.5° C., 18° C., 18.5° C., 19° C., 19.5° C., 20° C., 20.5° C., 21° C., 21.5° C., 22° C., 22.5° C., 23° C., 23.5° C., 24° C., 24.5° C., 25° C., 25.5° C., 26° C., 26.5° C., 27° C., 27.5° C., 28° C., 28.5° C., 29° C., 29.5° C., 30° C., 30.5° C., 31° C., 31.5° C., 32° C., 32.5° C., 33° C., 33.5° C., 34° C., 34.5° C., 35° C., 35.5° C., 36° C., 36.5° C., 37° C., 37.5° C., 38° C., 38.5° C., 39° C., 39.5° C., 40° C., 40.5° C., 41° C., 41.5° C., 42° C., 43.5° C., 44° C., 44.5° C., 45° C., 45.5° C., 46° C., 46.5° C., 47° C., 47.5° C., 48° C., 48.5° C., 49° C., 49.5° C., 50° C., and 50.5° C. per second. In a related embodiment said liquid metal or thermally conductive fluid heat block can change temperature at a rate substantially faster than conventional metal heat blocks while maintaining a uniform temperature across the heat block and/or within a sample within said heat block. In one embodiment the liquid metal heat block can increase temperature at a rate of at least 44° C. per second. In another embodiment the liquid metal heat block can decrease temperature at a rate of at least 17° C. per second. In one embodiment the temperature of the liquid metal or thermally conductive fluid is measured with glass bead thermistors (Betatherm). In another embodiment an infrared camera is used to measure the temperature of the liquid metal or thermally conductive fluid, or the liquid tight receptacle that covers the top of the heat block, or the temperature of the sample vessels. In another embodiment the temperature of the liquid metal or thermally conductive fluid is measured with an external probe. In yet another embodiment the temperature of the liquid metal or thermally conductive fluid is measured with a glass bead thermocouple. In another embodiment the temperature of at least one sample vessel is measured with a probe.

In some embodiments where the liquid metal or thermally conductive fluid heat block is used in a thermal cycler a series of PCR cycles may be performed faster than conventional solid block thermal cyclers. A single simple PCR cycle normally includes a denaturation step, a hybridization step and an extension step, each performed at a specific temperature. In some embodiments a series of 30 PCR cycles (PCR run) may be completed in 1 to 20 minutes, such as 1 min, 2 min, 3 min, 4 min, 5 min, 6 min, 7 min, 8 min, 9 min, 10 min, 11 min, 12 min, 13 min, 14 min, 15 min, 16 min, 17 min, 18 min, 19 min, 20 min. However, the length of time of a PCR run is dependent not only on the speed and temperature uniformity of the thermal cycler. It will be clear to a practitioner in the art that the length of time of the PCR run can be varied depending on the characteristic of the desired PCR product.

Compositions

Thermally conductive materials that are liquid at temperatures at which PCR is performed allow one to dip a sample vessel of any shape into the temperature control material and to maintain good thermal contact for heat transfer. Accordingly, the composition preferably is liquid at least in the range between primer annealing and duplex dissociation. Primer annealing occurs typically at around 55° C. but can be as high as about 70° C. or as low as about 45° C. Duplex dissociation occurs typically around 94° C. but can be lower depending on factors such as the length and percentage of guanine-cytosine base pairings (GC content) in the amplicon. Accordingly, in one embodiment the liquid composition has a melting temperature (i.e., transition from solid to liquid at) no greater than 70° C. In an alternative embodiment, the liquid composition has a melting temperature no greater than 60° C. In an alternative embodiment, the liquid composition has a melting temperature no greater than 50° C. In yet another embodiment, the liquid composition has a melting temperature no greater 40° C.

A variety of liquid metal compositions may be used in the practice of the claimed invention. In one embodiment the liquid metal composition may be gallium or a composition containing gallium. Some compositions may also comprise indium, copper, rhodium, silver, stannous, bismuth, tin and/or zinc. In one embodiment the liquid metal is obtained from Coollaboratory (Http://coolaboratory.com). In some embodiments the liquid metal may contain from 40-80% gallium and from 10-50% indium. In some embodiments the liquid metal alloy may contain from 1-40% copper, rhodium, silver, stannous, bismuth, tin, zinc or combinations thereof. In some embodiments the liquid metal alloy may comprise about 60% gallium/about 25.0% indium/about 14.0% Sn/about 1.0% Zn; about 62% gallium/22% indium/about 16.0% Sn; about 75% gallium/about 25% indium; about 95% gallium/about 5% indium; or 100% gallium. In a another embodiment the composition may contain 60-99% gallium in combination with indium, such as about 75% gallium and about 25% indium. An alloy with about 75% gallium and about 25% indium becomes a liquid at about 15.7° C. and has a boiling point of about 2,000° C. Such an alloy is in a liquid state but never reaches temperatures high enough to cause vaporization during PCR thermal cycling. Therefore even in embodiments where the liquid metal directly contacts the sample vessels toxicity due to vaporization of the liquid metal is not a problem.

In another embodiment a toxic liquid metal may be used in the present invention, such as mercury, mercury alloys or Woods metal. Woods metal which comprises about 50% Bi, 25% Pb, 12.5% Sn, 12.5% Cd has a high working temperature range (70-350° C.). A heat block comprising a liquid metal such as woods metal can be used to boil biological samples or in any other laboratory technique requiring a stable high temperature heat block.

In various embodiments, the liquid composition is a liquid metal, liquid metal alloy or metal containing slurry. The expansion coefficient of the liquid metal will vary according to the precise components of a liquid metal, metal alloy or slurry that are contemplated for use in thermal cyclers of the invention. In various embodiments, a liquid metal, liquid metal alloy or metal slurry it expands in volume during PCR by about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.5, 5.2, 5.3, 5.4, 5.5, 5.6, 5.7, 5.8, 5.9, or 6.0%, as compared to before PCR initiation.

In one embodiment a liquid metal, liquid metal alloy or metal containing slurry is designed to expand a sufficient amount to compress the junction between a container receptacle and a sample vessel, forming a tight contact. This contact provides enhanced thermal conductivity, as well as optical transmittance (e.g., reflectance of light back into the sample vessel). This tight contact increases the thermal conductivity between the liquid metal and the sample vessel by decreasing the air space separating the receptacle from the sample vessel. As one example, gallium exhibits a fairly uniform expansion.

TABLE 1

Gallium expansion

| Starting Temperature | End Temperature | Volume expansion |
|---|---|---|
| 25° C. | 55° C. | +1.08% |
| 55° C. | 72° C. | +0.61% |
| 72° C. | 95° C. | +0.83% |
| 25° C. | 95° C. | +2.54% |

In another embodiment the heat block comprise a liquid composition which is a thermally conductive fluid. A variety of thermally conductive fluids may be used in the claimed invention. The term thermally conductive fluids includes waxes and oils which have a working range of temperatures suitable for use in a thermal cycler. In other words the waxes and oils should have a relatively low melting temperature, in the range of 30-55° C. and maintain their stability at temperatures in at least in the range of 30-110° C. A variety of waxes and oils are suitable for use as thermally conductive fluids, including compounds such as, but not limited to hydrocarbon and silicon compounds and mixtures thereof. Examples include: silicone oil, carboxy-modified silicone oil, mineral oil, dibutyl phthalate, polydiethylsiloxanes, polydimethylsiloxanes, tetraalkoxysilanes, silahydrocarbons, polyalphaolefins, naphthenic oils, hydroisomerized oils, paraffinic oil, paraffin wax, paraffin wax, paraffin wax mixed with boron nitride, tricosane paraffin wax, polyorganosiloxane polymers, polyolefin wax, polyethylene wax or polypropylene wax and mixtures thereof. Further, the thermally conductive fluid may comprise additives which act to modify its stability, viscosity, expansion coefficient, opacity, and/or reflectivity. Such additives include but are not limited to plastics, minerals aqueous fluids, antifreezes or metals.

Reflectivity

In one embodiment a liquid metal or thermally conductive fluid is used that reflects substantially all of the light it receives. In another embodiment the liquid metal or thermally conductive fluid is a component in a heat block of a thermal cycler connected to an optical assembly that is capable of exciting fluorescent molecules in a sample vessel and detecting the signal. The sample vessels may be directly immersed in the liquid metal or thermally conductive fluid of the heat block, or be separated from the liquid metal or thermally conductive fluid by a receptacle that is thermally conductive. In embodiments comprising a receptacle, the receptacle may be manufactured with substantially transparent or reflective material. In these embodiments the liquid metal or thermally conductive fluid or reflective sample vessel surface reflects back substantially all of the light it receives which can then be detected by a light detection device, including but not limited to CCD devices, CMOS devices, LED devices, PN photodiodes, PIN photodiodes, or photovoltaic cells. Further, in embodiments where a transparent receptacle is used a transparent sample vessel may be used that consists of the same plastic as the receptacle, or is manufactured from a transparent material with a similar index of refraction as the receptacle.

In one embodiment the level of liquid metal or thermally conductive fluid is higher than the level of the sample in the sample vessel. In other words when viewed from the side, the volume of sample and PCR reaction cocktail in the sample vessel is below the level of the liquid metal or thermally conductive fluid. The liquid metal or thermally conductive fluid will then substantially reflect any light which enters or is created in the sample vessel. In one embodiment the liquid metal or thermally conductive fluid heat block is a component in a real time thermal cycler comprising an optical assembly comprising a multi-channel detection apparatus, such as multiple PIN diodes. For example the apparatus may comprise multiple single channels dedicated detecting light from individual wells in the receptacle. In this embodiment the liquid metal or thermally conductive fluid acts as an optical buffer which substantially prevents the light transmitted into or out of a first sample vessel from being detected by a detection channel associated with a second sample vessel.

Sample Vessels

The term "sample vessels" includes reaction vessels of a variety of shapes and configurations. In an embodiment sample vessels can be used to contain reaction mixtures, such as PCR reaction mixtures, reverse transcription reaction mixtures, real-time PCR reaction mixtures, or any other reaction mixture which requires heating, cooling or a stable uniform temperature. In one embodiment the sample vessels are round or tubular shaped vessels. In an alternative embodiment the sample vessels are oval vessels. In another embodiment the sample vessels are rectangular or square shaped vessels. Any of the preceding embodiments may further employ a tapered, rounded or flat bottom. In yet another embodiment the sample vessels are capillary tubes, such as clear glass capillary tubes or coated capillary tubes, wherein the coating (e.g. metal) increases internal reflectivity. In an additional embodiment the sample vessels are slides, such as glass slides. In another embodiment the sample vessels are sealed at the bottom. In one embodiment the sample vessels are coated, at least externally, with anti-adhesion coatings such as teflon or silane so as to reduce the adherence of a liquid composition, such as a liquid metal or thermally conductive fluid. In another embodiment the sample vessels are coated, at least internally, with a material for preventing an amplicon from sticking to the sample vessel walls, such as a fluorinated polymer or BSA.

In one embodiment the sample vessels are manufactured and used as individual vessels. In another embodiment the sample vessels are linked together in a horizontal series comprising a multiple of individual vessels, such as 2, 4, 6, 10, 12, 14 or 16 tubes. In yet another embodiment the sample vessels are linked together to form a sheet, plate or tray of vessels designed to fit into the top of the heating block of a thermal cycler so as to occupy some or all available reaction wells. In one embodiment the trays or sheets may comprise at least 6, wells, 12 wells, 24 wells, 36 wells, 48 wells, 54 wells, 60 wells, 66 wells, 72 wells, 78 wells, 84 wells, 90 wells or 96 wells, 144 wells, 192 wells, 384 wells, 768, or 1536 wells.

In one embodiment the sample vessels have caps attached to their open end by a linking element, such as a plastic strip which is optionally hinged. In another embodiment the sample vessels lack an attached cap. In one embodiment the sample vessels are designed to hold a maximum sample volume, such as 10 ul, 20 ul, 30 ul, 40 ul, 50 ul, 60 ul, 70 ul, 80 ul, 90 ul, 100 ul, 200 ul, 250 ul, 500 ul, 750 ul, 1000 ul, 1500 ul, 2000 ul, 5 mL, or 10 mL.

In some embodiments real-time polymerase chain reactions (PCR) are performed in sample vessels manufactured from materials chosen for their optical clarity and for their known non-interaction with the reactants, such as glass or plastic. In one embodiment the sample vessels are designed so that light can enter and leave through the top portion of the sample vessel, which may be covered a cap capable of transmitting light. In another embodiment the sample vessels are designed so that light can enter and leave the sample vessel through the bottom of the sample vessel. In one embodiment the sample vessels are manufactured from a transparent or translucent material capable of transmitting light. In one embodiment the sample vessels are designed so that light is directed to exit through a single surface, such as the top or bottom.

In other embodiments the sample vessels are manufactured from materials that are substantially internally reflective, such as reflective plastic, coated plastic (such as with metal or other reflective substances), coated glass (such as with metal or other reflective substances), doped glass (manufactured with the addition of molecules that increase the reflectivity of the glass), or metal, including but not limited to stainless steel, chromium, or other substantially non-reactive metals. Metal has a high strength that allows for much thinner sidewalls than glass or plastic. This decreases the thermal barrier between the reactants and external hot/cold sources, allowing for better thermal control, greater spatial temperature uniformity, and more rapid temperature changes, all of which can produce faster, more efficient polymerase chain reactions. In embodiments where epifluorescence is used to monitor real-time fluorescence, the high reflectivity of the internal metallic surface aids in the collection of fluorescent light. In one embodiment the interior of the metal sample vessels is polished or electro-polished.

Figure 13:
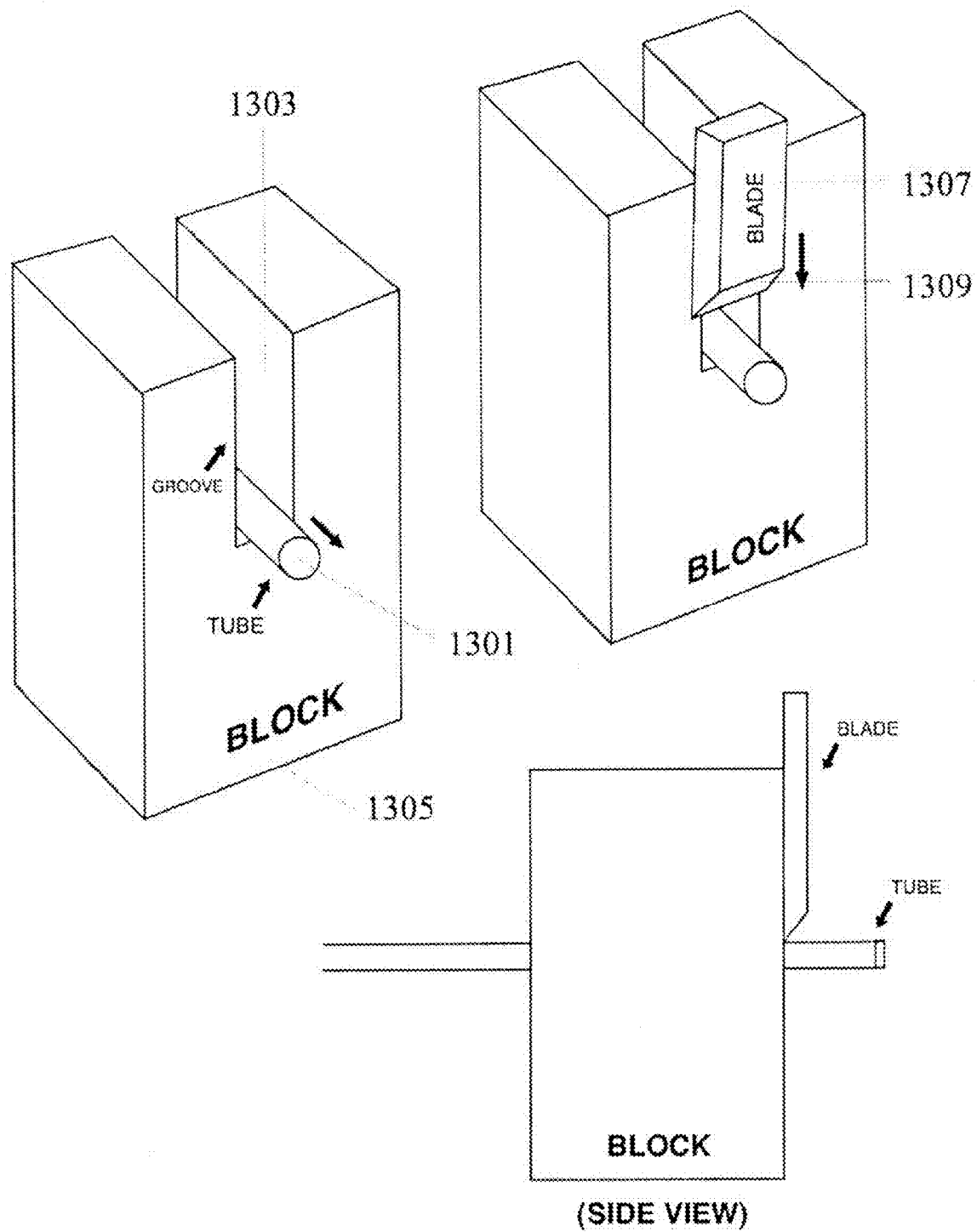
FIG. 13 illustrates a method of manufacture for metal sample vessels. This method can rapidly and inexpensively produce sample vessels by cutting and crimping them from a pulled metal stock in one movement. The groove is used to prevent the sample vessel walls from flaring out.

In one embodiment the metal sample vessels are manufactured from a larger cylindrical or rectangular stock. First the stock is pulled to the desired diameter. Alternatively the standard methods of syringe production may be used. A continuous tube (such as a rectangular or cylindrical tube) is generated, which must be both cut and sealed to produce pieces of a desired length., such as about 1 cM, 2 cM, 3 cM, 4 cM, 5 cM, 6 cM, 7 cM, 8 cm, 9 cM, 10 cM or any length in between. In one embodiment the diameter of the sealed end does not exceed the diameter of the tube itself. In this embodiment the tube is next cut and sealed: The tube (1301) may be fed through a groove (1303) in a metallic block (1305) (FIG. 13). In one embodiment the groove width is very close to the outer diameter size of the metal tube. As the tube (1301) exits the metal block (1305), a cutting blade (1307) is lowered with its edge flush with the metal block, perpendicular to the groove. In one embodiment the blade (1307) is shaped with a tapered edge (1309). In another embodiment the blade is shaped with an edge such that both cuts and crimps shut the end of the metal tube, and the groove walls prevent the seal from flaring, forcing its diameter to remain close to the diameter of the bulk tube. After crimping, the vessel may require further sealing. In one embodiment this can be accomplished with a small weld or braze or solder. In another embodiment cutting and crimping can be avoided by using a metal plug. If necessary the final sealed end can be ground to decrease its diameter and to remove rough edges.

In alternative embodiment, the metal sample vessel may be pulled to the desired diameter and cut into desired lengths. One end of each piece is then forced into a hemispherical cup having a similar diameter to the tube itself. This motion may round off and crimp closed the metal tube. In a related embodiment a pin is inserted through the open top of the metal tube to aid in crushing the seal end of the tube into the receiving cup. The tube can be crimp sealed in order to create a vessel with one closed end and one open end suitable for PCR.

Sample Vessel Caps

It is generally desirable to cover the top of the sample vessel to prevent evaporation during PCR thermal cycling. This can be accomplished by layering the top of the sample vessel with a layer of a non-reactive liquid, such as mineral oil, sealing the sample vessel (such as by heat sealing a capillary tube) or by closing the sample vessel with a cap.

In one embodiment a cap is used. The cap may be manufactured using any suitable material (such as glass or plastic) that forms a seal with the sample vessel and acts as a vapor barrier. In one embodiment the cap is a plastic cap. This cap may be opaque, translucent or substantially transparent. In one embodiment the cap is optically transparent and is suitable for use with a thermal cycler comprising a liquid metal or thermally conductive fluid heat block, and an optical assembly. In another embodiment the cap is partially or completely coated with an opaque coating. In yet another embodiment the cap is partially or completely coated with a reflective coating, such as a mirror coating.

The extraction of light from a sample vessel or vessel containing a material which fluoresces when pumped with an excitation wavelength can be difficult to accomplish especially when the heat block occludes the vessel. A sample vessel cap (303;403) which is made of a clear material, such as plastic or glass, and which optionally comprises a light-guide that can be optically coupled (with lenses, filters, beam splitters; e.g. FIG. 3) to a light source (such as a light emitter) and a detector, wherein the presence of the lightguide increases the amount of light delivered to the detector. The light emitter may be a coherent source such as a laser or a non-coherent source such as an LED.

In addition, an advantage of one of the exemplary embodiments of the invention is that light emitted from a label/dye in the sample vessel is reflected back into the sample vessel based on the reflective property of the liquid metal or thermally conductive fluid, liquid metal alloy or metal slurry. In a further embodiment, the amount of reflection is further enhanced by forming a better contact between the sample vessel and receptacle well (e.g., using the volume expansion to form a tight junction, or by using a pump to increase the pressure inside the liquid containing chamber, so that the liquid exerts additional pressure on the walls of the receptacle wells to form a tight junction with the sample vessels).

In another embodiment, a similar effect for light reflection is effected by utilizing the specialized sample vessels of the invention, where a sample vessel is comprised of an opaque composition (e.g., stainless steel) or is coated (internally/externally) with a opaque film (e.g., aluminum) that is reflective. In one embodiment the sample vessel is mirror coated. In embodiments wherein the sample vessel comprises metal, the metal may be polished or electro-polished to increases its reflectivity.

In either case, in various embodiments, cap implements of the invention are comprised of a material that is optically clear, characterized by having low or no autofluorescence and forms a good seal with the sample vessel. Furthermore, in some embodiments, the cap provides of an extrusion (e.g., lightguide) that protrudes a certain length into the sample vessel. Examples of material that can be utilized in composing the cap include but are not limited to acrylics, polycarbonates, polystyrenes, styrene block copolymers (SBCs), styrene acrylonitrile (SAN), ABS, polysulfones, thermoplastic polyesters (such as PET), polypropylene, acrylic-styrene copolymers (SMMA), PVC, nylon, cellulosic resins, cyclic olefin copolymers (COCs), allyl diglycol carbonate (ADC), Cyclic Olefins (such as TOPAS, ZEONOR and ZEONEX) and mixtures thereof.

In various embodiments, the cap and/or extrusion can be of a geometric shape which includes but is not limited to a polygon, elliptical, circle, square, rectangle, triangle, or any shape that can be obtained through injection molding (as known in the art). Furthermore, it will be recognized that the sample vessels, as well as the receptacle wells can also be of any of the shapes desired. In one embodiment, the cap, sample vessel, and receptacles are of the same geometric shape. In a further embodiment, the geometric shape is rectangular. In one embodiment, the geometric shape, is selected based on the material used in each of the cap, sample vessel and receptacle walls, so as to provide enhanced contact between the sample wall and receptacle wall, and provide optimum light transfer out of the sample vessel. In yet a further embodiment, the refractive index of the sample vessel wall and the receptacle wall is equal or nearly equal.

In one embodiment, the cap and cap extrusion are comprised of the same material. In one embodiment, the cap, cap extrusion, sample vessel and receptacle is each comprised of the same material or a different material, which are disclosed herein.

In some embodiments, the cap extrusion protrudes to a level in the sample vessel that is above, at or below the level (e.g., line) at which the liquid metal or thermally conductive fluid, liquid metal alloy or liquid metal slurry (collectively "liquid") is positioned. In one embodiment the protrusion is below the level of the liquid is positioned.

Figure 6:
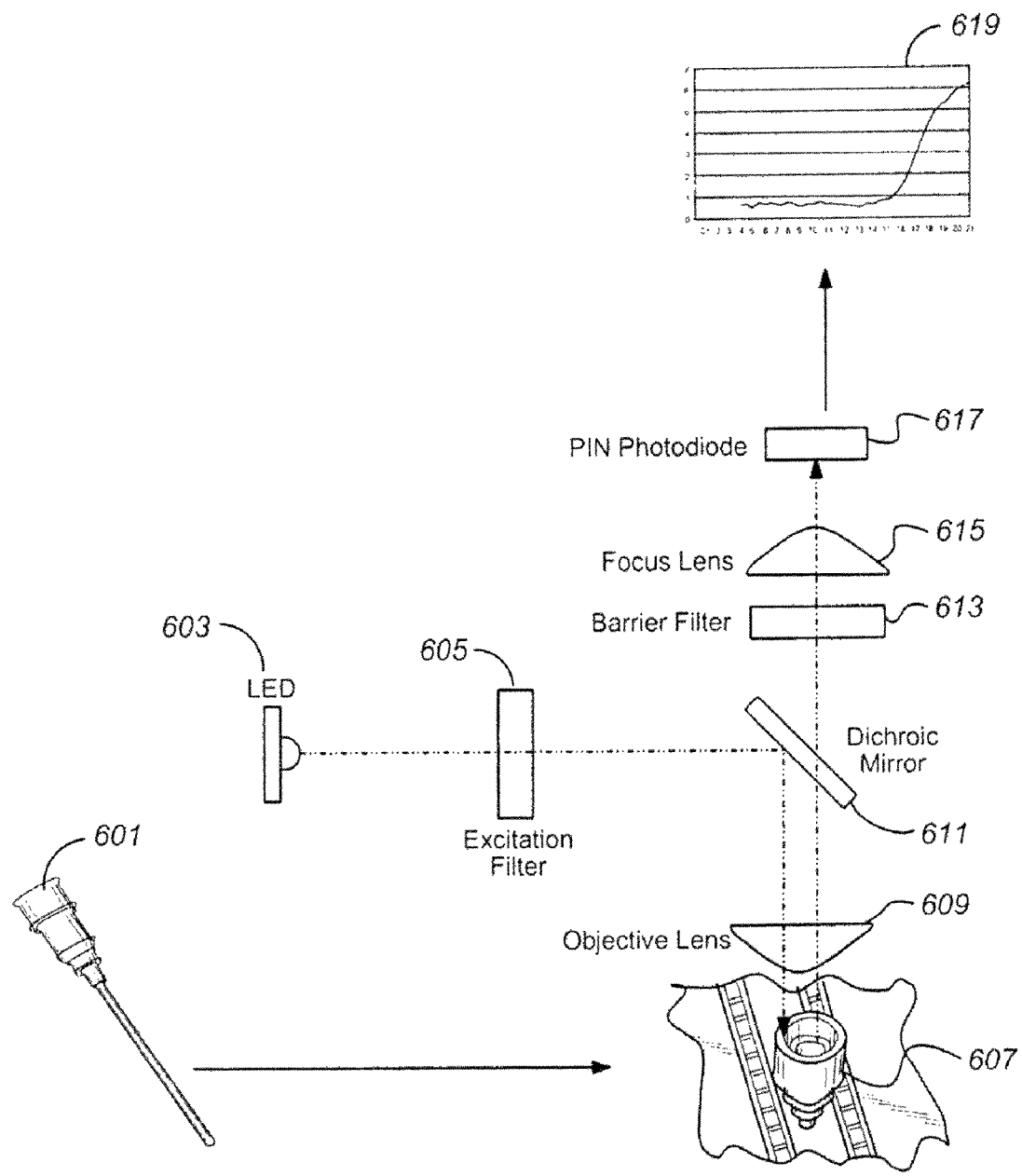
FIG. 6 illustrates an embodiment for detecting a signal from a sample vessel cycled in a heat block comprising a liquid metal composition. An LED is used to excite the sample contained within the sample vessel and any resulting signal is detected by a PIN photodiode.

In one embodiment, the light will travel the extrusion into the sample vessel and the resulting signal emitted from a label/dye in the sample travels back up the extrusion; this light is emitted from a substantially discrete portion of the cap where it is detected by a photodetector, such as a photodiode (e.g., FIG. 6).

In one embodiment the tip of the cap is below the surface level of the liquid metal or thermally conductive fluid. If viewed from the side it would be apparent that the tip of the cap was located below the level of the liquid metal or thermally conductive fluid in which the sample vessel was located so that it collects substantially all of the light. This is the case for embodiments where the sample vessel is directly immersed in the liquid metal or thermally conductive fluid as well as embodiments wherein the sample vessel is placed inside a receptacle well.

The cap shape and surface quality can be designed to maximize optical coupling from the cap into the liquid. In another embodiment the cap may be illuminated with a fiber bundle, or by a free space solution. The free space system may includes coupling lenses, and/or a beam splitter. The optical system may simultaneously excite the fluorescing liquid, and detect fluorescence.

In one embodiment the plastic cap may be fabricated either through cast plastic, or injection molding.

In one embodiment, the cap readily absorbs the heat emitted from the thermal cycler/liquid so that the cap is heated to a temperature that reduces or eliminates condensation. Often, with PCR methods in the prior art, the upper area/cap of a sample vessel would be at a cooler temperature than the lower portions of the sample vessel, thus reaction liquid would condense onto the colder surface thereby causing changes in the chemistry of the reaction (e.g., changes in concentrations leading to inefficient reactions or faulty results). In another embodiment the sample vessel is designed so that the sample vessel extends far enough below the surface level of the liquid so that the top entrance of the sample vessel is far enough from the surface of the sample/PCR cocktail that condensation is prevented. In yet another embodiment a lid or downward pressure on the cap forces the sample vessel into a tighter contact with the receptacle, which may retard evaporation.

Means for Heating and Cooling the Composition

The liquid metal or thermally conductive fluid heat block can be heated and cooled by using a variety of techniques known to a practitioner in the art. In one embodiment a heat block heating component is selected from a Peltier device, a resistive heater, and a radiative heater. In one embodiment, a heat block cooling component is a selected from a Peltier device, a heat sink, a refrigerator, an evaporative cooler, a heat pipe, a heat pump, and a phase change material. In one embodiment the heating element may provided by extending a tube into the heat block. The tube can be fitted with through which hot or cold fluids can be pumped. In some alternative embodiments the liquid metal or thermally conductive fluid heat block can be fitted with a heating and/or cooling coil, or with an electrical resistance heater arranged to prevent edge effects. In another embodiment the liquid metal or thermally conductive fluid heat block can be thermally coupled to a Peltier-effect thermoelectric device.

In one embodiment the heat block is designed so that the liquid metal or thermally conductive fluid maintains a uniform temperature throughout the block.

The Multi-Zone Heater Device

In one embodiment the liquid metal or thermally conductive fluid heat block is thermally coupled to a heating component, such as a multi-zone heater and a bias cooling system. In one embodiment the bias cooling system provides a small constant flow of chilled coolant through bias cooling channels in the attached to the base or sides of the heat block. This causes a constant, small heat loss from the heat block, which is compensated by a multi-zone heater. The heater is thermally coupled to the sample block for incubation segments where the temperature of the sample block maintained at a steady value. The constant small heat loss caused by the bias cooling flow allows the control system to implement proportional control both upward and downward in temperature in small increments. This means both heating and cooling at controlled, predictable, small rates is available to the temperature control system to correct for block temperature errors. The multi-zone heater may be controlled by a CPU.

Figure 10:
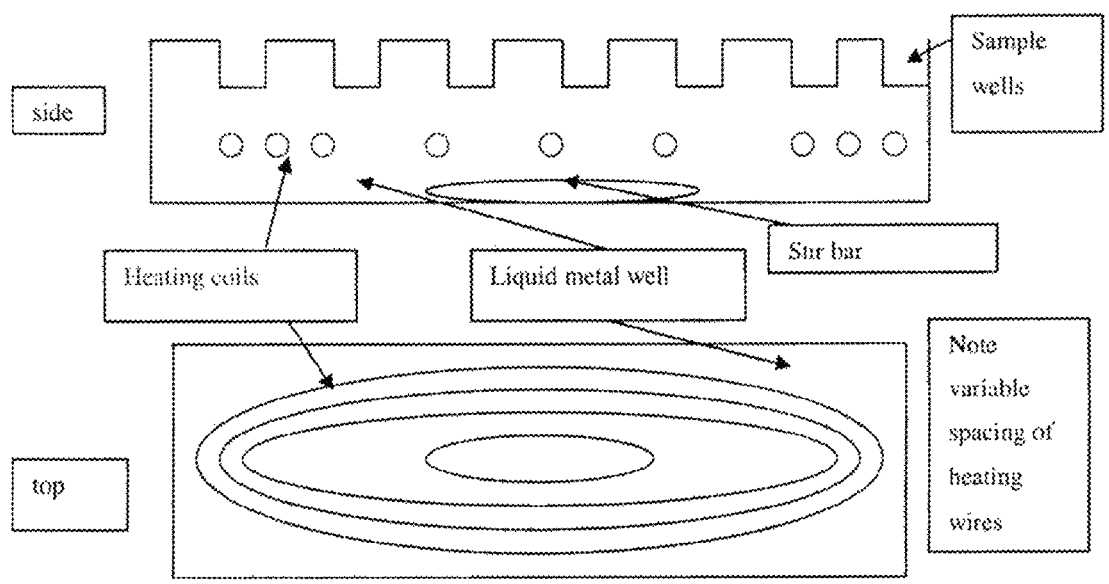
FIG. 10 illustrates an embodiment of the liquid composition heat block that uses resistive heating wires to heat the liquid composition. The top view shows wire arranged to provide uniform heating, wherein the wire are placed at a higher density near the edge of the liquid composition chamber and at a lower density near the center. This arrangement compensates for any possible edge effects which occur in conventional thermal cycler designs due to heat loss. As shown in the side view, the wires are suspended in the liquid composition, instead of resting on the bottom, such that liquid metal contacts the wires on all sides; this allows for maximum heat transfer uniformity.

In one embodiment, the heating element is comprised of one or more wire components, such as heat coils (FIG. 10). Such wire components are arranged to provide optimum heating and to reduce or eliminate edge effects. For example, the wire elements are arranged at the perimeter of the heating block. Furthermore, where a plurality of wire elements are utilized, they are spaced equidistantly, or in a increasing/decreasing distance gradient from the inside out to the outer perimeter to provide optimum heating and reduce or eliminate edge effects. In one embodiment the wires are arranged at the bottom of the block in a checkerboard pattern. In an alternative embodiment the wires are arranged in concentric circles or ovals along the bottom of the heat block. In another embodiment the wires are arranged along the base and sides of the heat block. In yet another embodiment the wires are arranged in pattern which allows the liquid metal to flow around all sides of the wires, such as a suspended, stacked or 3 dimensional arrangement comprising more than one checkerboard layer. In still another embodiment the wires are located more closely together near the edges of the heat block than in the interior of the heat block (such as variable spacing) so as to counteract the tendency of the outer edges of a heat block to cool at a faster rate than the interior (FIG. 10). It is known in the art that edge effects result in discordance in temperature uniformity, usually at the outer perimeters of thermal units.

In one embodiment a coolant control system continuously circulates a chilled liquid coolant such as a mixture of automobile antifreeze and water through bias cooling channels attached to the heat block via input and output tubes. The coolant control system also controls fluid flow through higher volume ramp cooling fluid flow paths in the heat block. The ramp cooling channels are used to rapidly change the temperature of the heat block by pumping large volumes of chilled liquid coolant through the block at a relatively high flow rate.

In one embodiment, the liquid coolant used to chill the heat block consists mainly of a mixture of water and ethylene glycol. The liquid coolant is chilled by a heat exchanger which receives liquid coolant which has extracted heat from the sample block via an input tube. The heat exchanger receives compressed liquid refrigerant (such as freon or ethanol) via an input tube from a refrigeration unit. This refrigeration unit generally includes a compressor, a fan and a fin tube heat radiator. The refrigeration unit compresses refrigerant received from the heat exchanger. The heated refrigerant is cooled and condensed to a liquid in the fin tube condenser. The pressure of the refrigerant is maintained above its vapor pressure in the fin tube condenser by a flow restrictor capillary tube. The output of this capillary tube is coupled to the input of the heat exchanger. In the heat exchanger, the pressure of the refrigerant is allowed to drop below its vapor pressure, allowing it to expand. In this process of expansion, heat is absorbed from the warmed liquid coolant circulating in the heat exchanger and this heat is transferred to the refrigerant thereby causing the refrigerant to boil. The warmed refrigerant is then extracted from the heat exchanger and is compressed and again circulated through the fin tube condenser. The fan blows air through the fin tube condenser to cause heat in the refrigerant from tube to be exchanged with the ambient air. In one embodiment the refrigeration is capable of extracting at least 400 watts of heat at 30° C. and 100 watts of heat at 10° C. from the liquid coolant to support the rapid temperature cycling.

In alternative embodiments, bias cooling may be eliminated or may be supplied by other means such as by the use of a cooling fan and cooling fins formed in the metal of the sample block, Peltier junctions or constantly circulating water (such as distilled or tap water).

Peltier-Effect Thermoelectric Device.

Peltier devices or elements, also known as thermoelectric (TE) modules, are small solid-state devices that function as heat pumps. A typical Peltier unit is a few millimeters thick by a few millimeters to a few centimeters square. It is a sandwich formed by two ceramic plates with an array of small Bismuth Telluride ($Bi_2Te_3$) cubes ("couples") in between. When a DC current is applied heat is moved from one side of the device to the other where it can be removed by a heat sink. The "cold" side may be used to cool an electronic device such as a microprocessor or a photodetector. If the current is reversed the device changes the direction in which the heat is moved. Peltier devices lack moving parts, do not require refrigerant, do not produce noise or vibration, are small in size, have a long life, and are capable of precision temperature control. Temperature control may be provided by using a temperature sensor feedback (such as a thermistor or a solid-state sensor) and a closed-loop control circuit, which may be based on a general purpose programmable computer.

In an alternative embodiment a thermal cycler comprises a liquid metal or thermally conductive fluid heat block thermally coupled to a heating component which is a Peltier element, in order to obtain a desired temperature profile (a temperature curve during a defined time interval) in the liquid metal or thermally conductive fluid heat block (FIGS. 1-4). In this embodiment the Peltier element, depending on the temperature to be obtained, is used as a cooling or a heating element within a temperature profile.

In another embodiment the thermal cycler may further comprise an electric resistance heater and a Peltier element used in combination to obtain the required speed of the temperature changes in the liquid metal or thermally conductive fluid heat block and the required precision and homogeneity of the temperature distribution.

In one embodiment the thermal cycler contains at least one Peltier element that forms part of the thermal cycler for cyclic alteration of the temperature of a heat block comprising a liquid composition. At least one heat transfer surface of the Peltier element is in thermal contact over a large area with the bottom surface of the liquid metal, heat block plate, or heat spreader and the other heat transfer surface is in contact over a large area with a cooling member for heat dissipation. The cooling member may be a metal such as aluminum or copper. The thermal cycler may further comprise a fan for heat dissipation which may be optionally switchable. In an alternative embodiment the liquid metal or thermally conductive fluid heat block and a Peltier element are joined to form a discrete unit (a swap block) which can be removed from the body of the thermal cycler. The swap block may further comprise a heat sink coupled to the Peltier element and/or a fan. This swap block can be removed from the thermal cycler for repair or to be replaced by a swap block with different functional elements, such as receptacles designed to hold sample vessels of a different size or shape than the previous swap block. Further as technological advances are made the swap blocks can be upgraded without purchasing an entirely new thermal cycler.

In another embodiment, a heat block comprising a liquid composition is thermally coupled to a plurality of Peltier devices situated adjacent one another on a first side of said heat block. In an alternative embodiment, a heat block comprising a liquid composition (501;551;571) is thermally coupled to a plurality of Peltier devices (503;553;573), wherein at least one Peltier device is situated on a first side of said reservoir and at least a second Peltier device is situated on a second side of said reservoir. In one embodiment at least one Peltier device from a commercially available source, such as Marlow Industrries or Nextreme Thermal Solutions is coupled to a heat block comprising a liquid composition (Nextreme Thermal Solutions; 3040 Cornwallis Road, P.O. Box 13981, Research Triangle Park, N.C. 27709-39810).

In one embodiment the Peltier element is protected from thermodynamic mechanical tension peaks by a central spring-biased securing means which presses the Peltier element and holds it against the heat block. The Peltier element may be resiliently clamped between the heat transfer surfaces of the heat block and the cooling member. The contact surface of the cooling member can be pressed, for example, by a pressure spring, or similar device, against the Peltier element. In one embodiment the spring tension can be adjusted via a screw, a spring washer and a ball and socket joint, which further increases the degrees of freedom of the cooling member.

In an alternative embodiment the Peltier element is used exclusively as a cold-producing (heat removal) element. That is, it is only used for cooling a heater unit. This will prolong the useful life of the Peltier element.

In another embodiment, the thermal cycler may incorporate an electric resistance heater disposed around the heat block and along the periphery of the outer wall of the heat block. In this embodiment the Peltier element may be used only for cooling. This relieves the Peltier element from mechanical thermal stress and thus contributes to prolonging the service life of the Peltier element in the thermal cycler.

Lids

In some embodiments the liquid metal or thermally conductive fluid heat block is part of a thermal cycler that optionally includes a lid, such as a hinged lid. In various embodiments, a lid can be fastened to the block by various means (e.g., clip, spring, screws, etc.). In one embodiment the lid contains a closing and pressing device for securing the sealed sample vessels positioned in the receptacle of the liquid metal or thermally conductive fluid heat block. In an alternative embodiment the lid may seal the sample vessels as it closes. A lid may have a spring held pressure plate, which presses each sample vessel with a defined force into the wells of the receptacle of the liquid metal or thermally conductive fluid heat block. The lid may further comprise recesses for holding the cap-shaped lids sample vessels and/or openings for piercing by pipetting needles in the pressure plate coaxially with the sample vessels. The spring element may comprise a corrugated washer. In one embodiment a safety ring prevents the pressure plate from falling out when the hinged lid is opened.

In another embodiment the lid comprises a heating element. In an alternative embodiment the lid of the thermal cycler, incorporates a detection mechanism capable of detecting light. This lid may further comprise a heating element. For some analyses, such as PCR, it is necessary to warm the receptacle to a controlled temperature. At the elevated temperature, the sample vessel contents tend to evaporate at a higher rate. To reduce evaporation and consequent loss of material from the receptacle, it may be covered with a cover which is heated to above the temperature of the samples in the sample vessels contained in the receptacle. In one embodiment the temperature of the cover is heated to a temperature at least 5° C. higher than the temperature of the sample vessel.

In one embodiment the heated lid comprises a cover that is sized to cover the entire top area of the receptacle. The lid may have at least two thin plates made of rigid, heat tolerant material, such as ceramics, glass, or silicon rubber. Sandwiched between the plates is an electrical resistive heating element, which in one embodiment may be in the form of a small diameter Nichrome wire or formed by depositing resistive materials such as Nichrome or stannous oxide on one of the plates. For example, a 36 gauge Nichrome wire with a resistivity of 12 Ohms per foot may be used to provide sufficient heating to the cover. The heating element may be configured in a serpentine fashion across the area of the plate so as to provide uniform heating across the cover. A filler material such as epoxy may be used to secure the plates and to fill the voids between the plates.

In a related embodiment the heating element is connected to a variable power supply, which can be controlled to provide current for heating the cover to a desired temperature. The leads between the power supply and the heating element may be flexible and configured to avoid stress in the leads so that the cover can be moved without restriction, e.g. by a robotic means in an automated laboratory workstation. A temperature sensor may be provided on the cover to measure its temperature and provide feedback for controlling the power supply for obtaining a desired temperature.

In an alternative embodiment it is contemplated that for situations in which the temperature of the sample vessels is below ambient temperature, it may be desirable to cool the cover to a temperature below ambient but above the temperature of the substance vapor. This is to maintain minimum temperature differential between the cover and the substance so that the temperature of the cover would not affect the controlled temperature of the substance in the receptacle.

Optical Assembly

In various aspects of the invention, the devices of the invention are configured to provide a means of measuring detectable labels in sample vessels comprising a reaction (e.g., real time PCR). Various embodiments of the devices of the invention are fully compatible with detection optics, so that rapid nucleic acid amplification/detection can be carried out. The thermal cyclers of the present invention by providing uniform temperature, rapid temperatures and increased signal reflectivity, during PCR or related processes, enable more accurate amplification, detection and measurement. As such, one advantage is that less expensive optical assemblies can be utilized with a thermal cycler of the invention, and yet obtain as accurate or more accurate real-time measurements. Therefore, a thermal cycler of the invention enables rapid, accurate, and reliable DNA amplification and detection, with less expensive optics, as well as conventional optic assemblies.

Optical measurement devices are known in the art. Generally, the measuring optic includes a light source, which for example is formed by a light emitting diode. The light source is directed toward the measuring field (e.g., sample vessel/tube). The light source is controlled by a evaluation and control circuit which can be operably linked to a computer, containing computer executable logic for controlling optic measurements. The measuring optic further includes a detector which can receive light from the entire measuring field. The detector is connected with the evaluation circuit/computer.

Optical assemblies useful in various embodiments of the invention comprise those having a CCD imager, a CMOS imager, a line scanner, at least one photodiode, at least one phototransistor, at least one photomultiplier tube, at least one avalanche photodiode, a microlaser, or a q-switched laser. In various embodiments, the reader can be a reflectance, transmission, epifluorescence/fluorescence, chemo-bioluminescence, magnetic or amperometry reader (or two or more combinations), PIN diode, or other readers known in the art depending on the signal that is to be detected from a sample tube.

In various embodiments, the light sources that can be coupled into an optical assembly of the invention include LEDs, laser diodes, VCSELs, VECSELs, DPSS lasers or fiber optic connections that can be subsequently coupled to light sources such as large laser systems, laser diodes or lamps. In another embodiment, the diode is a laser diode. Laser diodes can be used for illumination, photodiode detectors have excellent sensitivity, and most materials have minimal autofluorescence in the pertinent spectral region. Any conventional, LED or photodiode may be utilized, such as the PIN photodiodes from Pacific Silicon Sensors (5700 Corsa Avenue, Westlake Village Calif., 91362).

In various embodiments of the invention, optical assemblies are configured to provide excitation (light source)/emission (detector) at wavelengths such as: 365/460, 470/510, 530/555, 585/610, 625/660, 680/712 nm. Furthermore, in some embodiments, various filter windows are utilized at +−5-20 nm. Various fluorescence filter sets are commercially available (e.g., Omega Filters; Omega Optical, Inc.; or INTORR), including dye-specific filters for single or multi-label fluorescence.

In some embodiments, an optical assembly is configured with light sources having the specifications provided in Table 1:

| Color | Dominant wavelength (nm) or CCT (K) | | Typical Luminous or Radiant flux @ 700 mA |
|---|---|---|---|
| | Min. | Max. | |
| White | 4500K | 8000K | 76 lm |
| Royal Blue | 455 nm | 465 nm | 385 mW |
| Blue | 465 nm | 475 nm | 28 lm |
| Cyan | 500 nm | 510 nm | 75 lm |
| Green | 520 nm | 535 nm | 80 lm |
| Amber | 585 nm | 595 nm | 57 lm |
| Red-Orange | 610 nm | 620 nm | 86 lm |
| Red | 620 nm | 635 nm | 61 lm |

FIG. 3 provides one example of an optical assembly, where a PIN photodiode is the optical detector. For example, the optical assembly for detecting fluorescence comprises a light source 603 that provides lights passing through an excitation filter 605 which is directed into a sample vessel by a dichroic reflector/mirror 611 through an objective lens 609 which focuses the light beam into the sample vessel. The same lens collects fluorescence generated by the constituents of the sample (e.g., SYBR Green or Cy5; intercalating dyes disclosed herein), which emission passes the dichroic filter 611 and directed back up through a barrier filter 613, focus lens 615 and into the detector module PIN photodiode 617. The output is digitized and displayed as a graph electronically or displayed on paper or recorded 619. Furthermore, the use of epifluorescence provides an additional advantage in that there are no size constraints, thus a numeric aperture aspheric or ball-type lenses can be used as a collection optic.

In further embodiments, additional excitation filters can be positioned for increased spectral conditioning. In one embodiment, the light sources is a Cree XLamp and the optical detector is a T5 and/or T18 PIN diode.

In one embodiment, an optical assembly emits and detects light through the same portion of a sample vessel (e.g., cap). In another embodiment, an optical assembly light source emits light from one portion of a sample vessel (e.g., into a PCR reaction), while emissions are detected from another portion of the sample vessel (e.g., where light source is at bottom and detector is at top, or vice versa).

In one embodiment, the reader is a LED reader which detects a fluorescence signal. The fluorescence signal is excited by a light emitting diode that emits in the region of the optical spectrum and within the absorbance peak of the signal (e.g., fluorescent label). The emitted fluorescence signal is detected by a photodiode. Furthermore, the wavelength of the signal detected may be limited using a long pass filter which blocks stray emitted light and transmits light with wavelengths at and above the peak emission wavelength of the fluorescence emitting label. In other embodiments, the long pass filter may be replaced by a band pass filter. Furthermore, the excitation light may be limited by a band pass filter.

In some embodiments the excitation source and the detector are mounted in a single machine (such as the body of a thermal cycler), molded block (e.g., FIGS. 1-2), for simplified reading of the fluorescent signals generated in the sample tubes.

For example, Cy5 is a popular red-emitting fluorophore with a very high extinction coefficient. Common forms of such a fluorophore include the N-hydroxysuccinimide ester of or the related dye, Cy5.5. These dyes are indodicarbocyanine dyes that are used commonly in flow cytometry and automated fluorescence sequencers and are available from Amersham (Pittsburgh, Pa.). Cy5 is commercially available as amidites for direct, automated incorporation into oligonucleotides. In one embodiment, samples labeled with Cy5 are processed utilizing the devices of the invention. For example, working in the red/infrared region of the spectrum is advantageous when choosing optical components for instrumentation.

In another example real-time measurements of PCR amplification can be made utilizing SYBR Green. However, it should be noted that as desired, in some embodiments, any of the various labels/dyes known in the art or disclosed herein can be utilized in thermal cycler devices of the invention (e.g., SYBR Green, Q-dots, etc.).

In various embodiments of the invention, a system comprising a cycle of the invention further comprises a collection of photodetectors, in which each photodetector provides an output signal. The system also comprises at least one light source. The light source is positioned such that light emitted passes through a corresponding well retained in or otherwise provided by a multi-well plate (305;405) or strip of sample vessels and to a corresponding photodetector or a collection of photodetectors. The system also includes a processor or other means for analyzing the output signals from the plurality of photodetectors. In an alternative embodiment, the devices of the invention obviate the need to utilize expensive fluorochromes or dye markers, which require large integrated light sources and detection optics on the system. For example, an integrated real-time PCR system can cost $90,000 (Applied Biosystems ABI PRISM® 7700 Sequence Detection System) as compared to $7,500 for a non-real time PCR system (GeneAmp 9700). Both systems perform PCR amplification for 96 well plates but the GeneAmp 9700 requires a separate spectrophotometer or a fluorescent well plate reader for DNA concentration measurement.

Since the footprint of an LED or laser diode is very small, multiple LEDs or lasers of different wavelength could be integrated into a single package or several packaged LEDs/laser can be very closely spaced to excite one well/sample tube.

In some embodiments, the LED actually represents several LEDs with different wavelengths, but very closely spaced. Therefore, in further embodiments, the detectors are similarly configured.

In some embodiments, light sources for optics configurations of the invention can be an LED or a laser diode. Other light sources can be utilized. Furthermore, the number of light sources used in association with each well may vary. In one non limiting example of using devices of the invention, an LED is activated to emit light of a first wavelength or first set of wavelengths, which excites a dye or label in a sample that which emits a signal. The signal is detected by the appropriate photodetector and then, or concurrently, a second LED is activated, which emits light having a different wavelength or set of wavelengths from the first LED. This light excites a different dye or label in a sample, which emits a signal that is detected by the appropriate photodetector. The second LED is de-activated and then, or concurrently, a third LED is activated. The third LED emits light having a different wavelength or set of wavelengths from the first LED and second LED. This light excites a different dye or label in a sample, which emits a signal that is detected by the appropriate photodetector. These measurements are performed very rapidly and processed by a computer generated display. The collection of closely spaced light sources can be configured to sequentially emit light as described.

In other embodiments, different light sources are configured in the optical assembly and separately detected using optical detectors, wherein detection is at the same time.

In one embodiment, the devices of the invention are configured with an array of light sources and light detectors. It will be understood that the light source array includes a plurality of light sources disposed on a suitable substrate or mounting component and arranged in a particular configuration, which typically is a grid pattern. The well array comprises a plurality of sample wells (FIG. 1,2), also supported and positioned on or within a suitable retaining substrate. The photodetector array includes a plurality of photodetectors similarly mounted and arranged to receive light emitted from an array of sample vessels (305;405) such as through sample vessel caps (303;403) (FIG. 3).

In some embodiments, a rail system comprising multiple separate light sources (of the same or multiple different wavelengths) can be configured over a row of samples in a multi-row arrangement, along with the corresponding number of detectors. For example, the number of light sources and corresponding detectors can be 8 separate light sources of perhaps multiple wavelengths, detected by 8 different detector setup each which can detect multiple wavelengths emitted from an excited sample. Therefore, the rail system can be operated to move back and forth interrogating successive rows of sample vessels. Various commercially available filters can be utilized as described herein above. In one embodiment the detectors comprise optics made cheaply through injection molding.

In some embodiments, higher power LED's can be used. Avalanche photodiodes, e.g. SiC, GaN, GaAs or Si or blue enhance Si photodiodes can also be used. The sensitivity of avalanche photodiodes is much greater than simple photodiodes because the signal is amplified by the avalanche process. Avalanche photodiodes have a typical gain of between 10 and 10000, which means that the signal is amplified by a factor of 10 to 10000. Using improved measurement techniques like lock-in amplifiers can also extend the dynamic range of the measurements.

In one embodiment of a PCR system utilizing light sources and particularly the use of LED for the emission of such light, provides new possibilities and applications. In one embodiment, an LED light source contemplated is a GaN-based ultra-violet LED. In another embodiment, the light source is cree xlamp 750 mwatt ultra bright LEDs.

In one embodiment, a single wavelength emission is utilized. No additional grating or filter or complex optics are required to select the desired wavelength and focus the light. That significantly simplifies the experimental setup and reduces the cost of assembly. Another advantage is the low cost of LED's. Semiconductor LED's can be mass-produced and made extremely inexpensive. Current GaN-based violet, blue and green LED's cost on the order of 10 to 50 cents per packaged device and a similar price range is to be expected for future mass-produced GaN-based LED's. Multiple wavelength LED's can be either integrated as hybrid LED chips or special LED's could be developed, whose emission can be switched between two or more wavelengths.

Yet another advantage relates to the high output power of LED's. LED's output power levels in the range of 10 mW are within reach in the near future. Furthermore, the typical footprint of an LED is 200 um×200 um, which means that the light intensity can be concentrated to a smaller area and reduces the amount of additional optics (e.g. lenses) needed to concentrate the light. That is a considerable advantage for high throughput PCR systems with a large number of wells per plate (48, 96, 384, or 1536 wells) and consequently smaller wells. Even with 48, 96 or 384 wells, well dimensions are still large enough to fit several LEDs in the area of a single well in a well plate.

Furthermore, another advantage relates to LED arrays. Multiple LED's can also be arranged in one- or two-dimensional LED arrays. This enables the measurement of the fluorescence in multiple wells at the same time. Massive parallel processing significantly reduces the measurement time and accelerates the throughput. This can be a significant cost/time factor in the operation of a PCR system, particularly with the trend going to higher-density well plates.

Moreover, another advantage of LED's is that these light sources can be pulsed. In order to avoid bleaching or heating of the DNA molecules; short, but intense pulses can be produced by LED's. LED's can be turned on and off in a very short time scale (about 1 ns to 100 ns), depending on the design, the size and the packaging of the LED. The LED pulses can also be synchronized with a photodetector readout using common lock-in techniques to achieve better signal to noise ratios and higher sensitivity ranges. In addition, LED's do not require any warm-up time before stable light output is achieved. This is in contrast to deuterium and Xenon lamps, which require at least several minutes of warm-up time, before stable operation is achieved.

Yet another advantage in using an LED light emitting source is the relatively long operating lives of such components. It is believed that the operating life of an LED may be as long as 10,000 or more hours. The use of these light sources would eliminate replacement of the LED in most systems.

In one embodiment, a method of performing a polymerase chain reaction assay with fluorescence detection is provided. The method comprises providing a system that includes a multi-well plate, a thermal cycler, a photodetector that provides an output signal, at least one light source positioned to pass light through the multi-well plate and to the photodetector, and a means for analyzing the output signal of the photodetector. The method also comprises obtaining samples upon which the polymerase chain reaction assay is to be performed. Additionally, the method comprises depositing samples in the multi-well plate. And, the method comprises performing a polymerase chain reaction in the samples. The method includes emitting light from the light source(s) such that light passes through the samples to the photodetector. And, the method comprises analyzing the output of the photodetector to determine the absorbance of emitted fluorescent light and information indicative of the polymerase chain reaction.

In another embodiment the fluorescence emitted by a sample after PCR was performed in a thermal cycler comprising a heat block comprising a liquid composition is detected using rough detection. In an embodiment the rough detection does not quantitate the amount of an amplification product or amplicon, but instead only detects the presence or absence of said amplification product. Rough detection may be performed using inexpensive optics or detectors, with few or no filters and/or plastic lens. In one embodiment only a photodiode or LED detector is used. In another embodiment, fluorescence is detected using a filterless system, such as time resolved fluorescence (TRF). In one aspect the light source (LED or laser diode) is turned off, and the fluorescent molecules continue to emit light for a short but measurable amount of time; this emitted light can be measured without having to filter out the LED/laser light.

In yet another embodiment a detection system is used with FRET-based probes. In an embodiment, the detection system is capable of detecting two different wavelengths nearly simultaneously. With FRET probes, two fluorophores are located on the probe. A sample comprising the probe is stimulated with a single excitation light source. The light source is of a wavelength that stimulates a first fluorophore, which emits light, the majority of which is absorbed by the second, neighboring fluorophore. The second fluorophore emits light at a wavelength different from the first fluorophore. Both of these signals are then detected.

In accordance with yet another aspect of the present exemplary embodiment, a method of performing a polymerase chain reaction assay is provided. The method is based upon using light as follows. The method includes providing a system including (i) a multi-well plate adapted to retain a plurality of samples, (ii) a thermal cycler, (iii) a photodetector that provides an output signal, (iv) a plurality of light sources positioned such that light emitted passes through the multi-well plate to the photodetector, and (v) a means for analyzing the output signal of the photodetector upon detecting ultraviolet light. The method also comprises obtaining samples upon which the polymerase chain reaction assay is to be performed. The method further comprises depositing the samples in the multi-well plate. The method also comprises performing a polymerase chain reaction in the samples. The method further comprises emitting light from the plurality of light sources such that the light passes through the samples to the photodetector. The method also includes analyzing the output signal of the photodetector.

In various embodiments turn on/off times for LEDs are typically on the order of a few nanoseconds or tens of nanoseconds. In other embodiments, laser diodes are even faster with sub nanosecond switching times.

In an alternative embodiment, a PCR system is provided and related assays and techniques that do not require the use of fluorophores and associated detection light sources and optics otherwise required. For example, LED could contain a 260 nm and a 280 nm LED. To perform an absorbance measurement, first the 260 nm LED would be turned on and the absorbed light at 260 nm detected by the photodetector. The 260 nm LED would be turned off and then the 280 nm would be turned on and the absorbed light at 280 nm detected by the photodetector. These measurements could be performed very quickly after each other since they do not require any physical movement of the sample LEDs can be turned on and off very quickly. Therefore, in one alternative embodiment the optical configuration can reduce the cost of fluorescent primers and Taqman probes utilized with many real-time PCR systems.

In one embodiment, an array of inexpensive ultra-violet LED's, emitting 260 nm and 280 nm wavelength light are incorporated in a PCR system with the format of a well plate in thermal contact (directly/indirectly) with a liquid medium (e.g., liquid metal or a thermal fluid). The arrays of emitter and detectors have a configuration, that may correspond to the arrangement of sample vessels in the liquid composition heat block of the thermal cycler, for example, like the sample vessels (305;405) in FIG. 3. Thus, a plurality of ultra-violet light emitting units, such as LED's are positioned with respect to a plurality of wells FIG. 1, such that light emitted from each LED travels through a corresponding well (and sample contained therein), and is received by a corresponding photoreceptor or photodetector. Optical filters could be used, either placed at the input of the photodetector or at the output of the LEDs/lasers or both to suppress any unwanted light (e.g. light emitted by the LED aside from the center wavelength peak) FIG. 3. For example, LEDs sometimes exhibit luminescence at longer wavelengths from recombination through defects in the LEDs active regions or recombination of carriers outside the active region of the LED. This unwanted luminescence is typically 3 to 4 orders smaller than the main luminescence peak. Nevertheless it may be desirable to suppress this luminescence even further by using optical band-pass filters.

In various embodiments optical assembly systems known in the art can be configured for use with a thermal cycler device of the invention. Examples of such optical assemblies as well as reagents useful in detecting reaction products are disclosed in US Patent Application Nos. 2006/0134644, 2006/0014200, 2005/0255516, 2005/0237524, 2005/0136448, 2004/0133724, 2003/0059822, 2002/0034746 and U.S. Pat. Nos. 7,101,509, 6,942,971, 6,940,598, 6,911,327, 6,783,934, 6,713,297, 6,403,037, 6,369,893, 7,122,799, 7,113,624, 6,037,130, 5,792,610, 5,440,388, 6,873,417, 6,998,598, 6,437,345, 53,011,059, and 6,388,799, the disclosures of each of which is incorporated by reference herein in its entirety.

Control Assembly

In various embodiments a control assembly is operatively linked to a thermal cycler of the invention. Such a control assembly, for example, comprises a programmable computer comprising computer executable logic that functions to operate any aspect of the devices, methods and/or systems of the invention. For example, the control assembly can turn on/off motors, fans, heating components, stir bars, continuous flow devices and optical assemblies. The control assembly can be programmed to automatically process samples, run multiple PCR cycles, obtain measurements, digitize measurements into data, convert data into charts/graphs and report.

Computers for controlling instrumentation, recording signals, processing and analyzing signals or data can be any of a personal computer (PC), digital computers, a microprocessor based computer, a portable computer, or other type of processing device. Generally, a computer comprises a central processing unit, a storage or memory unit that can record and read information and programs using machine-readable storage media, a communication terminal such as a wired communication device or a wireless communication device, an output device such as a display terminal, and an input device such as a keyboard. The display terminal can be a touch screen display, in which case it can function as both a display device and an input device. Different and/or additional input devices can be present such as a pointing device, such as a mouse or a joystick, and different or additional output devices can be present such as an enunciator, for example a speaker, a second display, or a printer. The computer can run any one of a variety of operating systems, such as for example, any one of several versions of Windows, or of MacOS, or of Unix, or of Linux.

In some embodiments, the control assembly executes the necessary programs to digitize the signals detected and measured from reaction vessels and process the data into a readable form (e.g., table, chart, grid, graph or other output known in the art). Such a form can be displayed or recorded electronically or provided in a paper format.

In some embodiments, the control assembly controls circuitry linked to the thermal elements so as to regulate/control cycles temperatures of a thermal cycler of the invention.

In further, embodiments, the control assembly generates the sampling strobes of the optical assembly, the rate of which is programmed to run automatically. Of course it will be apparent, that such timing is adjustable for shining a light sources and operating a detector to detect and measure signals (e.g., fluorescence).

In another embodiment an apparatus comprising a control assembly further comprises a means for moving sample vessels into apertures, such as wells in the receptacle of a heat block comprising a liquid composition. In an embodiment said means could be a robotic system comprising motors, pulleys, clamps and other structures necessary for moving sample vessels.

Sample preparation station. In some aspects of the invention, the devices/systems of the invention are operatively linked to a robotics sample preparation and/or sample processing unit. For example, a control assembly can provide a program to operate automated collection of samples, adding of reagents to collection tubes, processing/extracting nucleic acids from said tubes, optionally transferring samples to new tubes, adding necessary reagents for a subsequent reaction (e.g., PCR or sequencing), and transferring samples to a thermal cycler, which are described herein. In various embodiments, the sample preparation can be in a continuous flow PCR system described herein (FIG. 11) or in a non-continuous systems (FIG. 1, 5).

Methods of Performing PCR

A thermal cycler comprising a liquid metal or a thermally conductive fluid heat block can be used for disease diagnosis, drug screening, genotyping individuals, phylogenetic classification, environmental surveillance, parental and forensic identification amongst other uses. Further, nucleic acids can be obtained from any source for experimentation using a liquid metal or a thermally conductive fluid heat block. For example, a test sample can be biological and/or environmental samples. Biological samples may be derived from human, other animals, or plants, body fluid, solid tissue samples, tissue cultures or cells derived therefrom and the progeny thereof, sections or smears prepared from any of these sources, or any other samples suspected to contain the target nucleic acids. Exemplary biological samples are body fluids including but not limited to blood, urine, spinal fluid, cerebrospinal fluid, sinovial fluid, semen, and saliva. Other types of biological sample may include food products and ingredients such as vegetables, dairy items, meat, meat by-products, and waste. Environmental samples are derived from environmental material including but not limited to soil, water, sewage, cosmetic, agricultural, industrial samples, air filter samples, and air conditioning samples.

A thermal cycler comprising a liquid metal or a thermally conductive fluid heat block can be used in any protocol or experiment that requires either thermal cycling or a heat block that can accurately maintain a uniform temperature. For example said thermal cycler can be used for polymerase chain reaction (PCR), quantitative polymerase chain reaction (qPCR), nucleic acid sequencing, ligase chain polymerase chain reaction (LCR-PCR), reverse transcription PCR reaction (RT-PCR), single base extension reaction (SBE), multiplex single base extension reaction (MSBE), reverse transcription, and nucleic acid ligation.

The apparatus of this invention allows one to perform PCR with increased speed and specificity, particularly in the context of real time PCR. The use of a composition with high thermal conductivity, such as a liquid metal, allows one to perform temperature ramping (both up and down) much faster than traditional PCR. This not only increases the potential speed at which one can carry out PCR, but it also increases the specificity of PCR by decreasing the incidence of non-specific hybridization of primers. Furthermore, in the context of real time PCR, measuring signal from a discrete portion of the test receptacle, such as the top, relieves one of the need to remove sample vessels from the heating composition for measurement. This also preserves temperature control and allows measurements to be made in real time with the heating cycles. The use of a reflecting material that prevents escape of signal except from the discrete location allows less sensitive detectors to be used as more light can be collected for measurement.

PCR reaction conditions typically comprise either two or three step cycles. Two step cycles have a denaturation step followed by a hybridization/elongation step. Three step cycles comprise a denaturation step followed by a hybridization step during which the primer hybridizes to the strands of DNA, followed by a separate elongation step. The polymerase reactions are incubated under conditions in which the primers hybridize to the target sequences and are extended by a polymerase. The amplification reaction cycle conditions are selected so that the primers hybridize specifically to the target sequence and are extended.

Successful PCR amplification requires high yield, high selectivity, and a controlled reaction rate at each step. Yield, selectivity, and reaction rate generally depend on the temperature, and optimal temperatures depend on the composition and length of the polynucleotide, enzymes and other components in the reaction system. In addition, different temperatures may be optimal for different steps. Optimal reaction conditions may vary, depending on the target sequence and the composition of the primer. Thermal cyclers may be programmed by selecting temperatures to be maintained, time durations for each cycle, number of cycles, rate of temperature change and the like.

Primers for amplification reactions can be designed according to known algorithms. For example, algorithms implemented in commercially available or custom software can be used to design primers for amplifying desired target sequences. Typically, primers can range are from least 12 bases, more often 15, 18, or 20 bases in length but can range up to 50+ bases in length. Primers are typically designed so that all of the primers participating in a particular reaction have melting temperatures that are within at least 5° C., and more typically within 2° C. of each other. Primers are further designed to avoid priming on themselves or each other. Primer concentration should be sufficient to bind to the amount of target sequences that are amplified so as to provide an accurate assessment of the quantity of amplified sequence. Those of skill in the art will recognize that the amount of concentration of primer will vary according to the binding affinity of the primers as well as the quantity of sequence to be bound. Typical primer concentrations will range from 0.01 uM to 0.5 uM.

In one embodiment, the liquid metal or thermally conductive fluid heating block may be used for PCR, either as part of a thermal cycler or as a heat block used to maintain a single temperature. In a typical PCR cycle, a sample comprising a DNA polynucleotide and a PCR reaction cocktail is denatured by treatment in a liquid metal or thermally conductive fluid heat block at about 90-98° C. for 10-90 seconds. The denatured polynucleotide is then hybridized to oligonucleotide primers by treatment in a liquid metal or thermally conductive fluid heat block at a temperature of about 30-65° C. for 1-2 minutes Chain extension then occurs by the action of a DNA polymerase on the polynucleotide annealed to the oligonucleotide primer. This reaction occurs at a temperature of about 70-75° C. for 30 seconds to 5 minutes in the liquid metal or thermally conductive fluid heat block. Any desired number of PCR cycles may be carried out depending on variables including but not limited to the amount of the initial DNA polynucleotide, the length of the desired product and primer stringency.

In another embodiment, the PCR cycle comprises denaturation of the DNA polynucleotide at a temperature of 94° C. for about 1 minute. The hybridization of the oligonucleotide to the denatured polynucleotide occurs at a temperature of about 37°-65° C. for about one minute. The polymerase reaction is carried out for about one minute at about 72° C. All reactions are carried out in a multiwell plate which is inserted into the wells of a receptacle in a liquid metal or thermally conductive fluid heat block. About 30 PCR cycles are performed. The above temperature ranges and the other numbers are not intended to limit the scope of the invention. These ranges are dependant on other factors such as the type of enzyme, the type of container or plate, the type of biological sample, the size of samples, etc. One of ordinary skill in the art will recognize that the temperatures, time durations and cycle number can readily be modified as necessary.

Reverse Transcription PCR

Revere transcription refers to the process by which mRNA is copied to cDNA by a reverse transcriptase (such as Moloney murine leukemia virus (MIVILV) transcriptase Avian myeloblastosis virus (AMV) transcriptase or a variant thereof) composed using an oligo dT primer or a random oligomers (such as a random hexamer or octamer). In real-time PCR, a reverse transcriptase that has an endo H activity is typically used. This removes the mRNA allowing the second strand of DNA to be formed. Reverse transcription typically occurs as a single step before PCR. In one embodiment the RT reaction is performed in a liquid metal or thermally conductive fluid heat block by incubating an RNA sample a transcriptase the necessary buffers and components for about an hour at about 37° C., followed by incubation for about 15 minutes at about 45° C. followed by incubation at about 95° C. The cDNA product is then removed and used as a template for PCR. In an alternative embodiment the RT step is followed sequentially by the PCR step, for example in a one-step PCR protocol. In this embodiment all of the reaction components are present in the sample vessel for the RT step and the PCR step. However, the DNA polymerase is blocked from activity until it is activated by an extended incubation at 95° C. for 5-10 minutes. In one embodiment the DNA polymerase is blocked from activity by the presence of a blocking antibody that is permanently inactivated during the 95° C. incubation step.

Real Time PCR

In molecular biology, real-time polymerase chain reaction, also called quantitative real time polymerase chain reaction (QRT-PCR) or kinetic polymerase chain reaction, is used to simultaneously quantify and amplify a specific part of a given DNA molecule. It is used to determine whether or not a specific sequence is present in the sample; and if it is present, the number of copies in the sample. It is the real-time version of quantitative polymerase chain reaction (Q-PCR), itself a modification of polymerase chain reaction.

The procedure follows the general pattern of polymerase chain reaction, but the DNA is quantified after each round of amplification; this is the "real-time" aspect of it. In one embodiment the DNA is quantified by the use of fluorescent dyes that intercalate with double-strand DNA. In an alternative embodiment modified DNA oligonucleotide probes that fluoresce when hybridized with a complementary DNA are used to quantify the DNA.

In another embodiment real-time polymerase chain reaction is combined with reverse transcription polymerase chain reaction to quantify low abundance messenger RNA (mRNA), enabling a researcher to quantify relative gene expression at a particular time, or in a particular cell or tissue type.

In certain embodiments, the amplified products are directly visualized with detectable label such as a fluorescent DNA-binding dye. In one embodiment the amplified products are quantified using an intercalating dye, including but not limited to SYBR green, SYBR blue, DAPI, propidium iodine, Hoeste, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin. For example, a DNA binding dye such as SYBR Green binds all double stranded (ds)DNA and an increase in fluorescence intensity is measured, thus allowing initial concentrations to be determined. A standard PCR reaction cocktail is prepared as usual, with the addition of fluorescent dsDNA dye and added to a sample. The reaction is then run in a liquid heatblock thermal cycler, and after each cycle, the levels of fluorescence are measured with a camera. The dye fluoresces much more strongly when bound to the dsDNA (i.e. PCR product). Because the amount of the dye intercalated into the double-stranded DNA molecules is typically proportional to the amount of the amplified DNA products, one can conveniently determine the amount of the amplified products by quantifying the fluorescence of the intercalated dye using the optical systems of the present invention or other suitable instrument in the art. When referenced to a standard dilution, the dsDNA concentration in the PCR can be determined. In some embodiments the results obtained for a sequence of interest may be normalized against a stably expressed gene ("housekeeping gene") such as actin, GAPDH, or 18s rRNA.

In various embodiments, labels/dyes detected by systems or devices of the invention. The term "label" or "dye" refers to any substance which is capable of producing a signal that is detectable by visual or instrumental means. Various labels suitable for use in the present invention include labels which produce signals through either chemical or physical means, such as flourescent dyes, chromophores, electrochemical moieties, enzymes, radioactive moieties, phosphorescent groups, fluorescent moieties, chemiluminescent moieties, or quantum dots, or more particularly, radiolabels, fluorophore-labels, quantum dot-labels, chromophore-labels, enzyme-labels, affinity ligand-labels, electromagnetic spin labels, heavy atom labels, probes labeled with nanoparticle light scattering labels or other nanoparticles, fluorescein isothiocyanate (FITC), TRITC, rhodamine, tetramethylrhodamine, R-phycoerythrin, Cy-3, Cy-5, Cy-7, Texas Red, Phar-Red, allophycocyanin (APC), probes such as Taqman probes, TaqMan Tamara probes, TaqMan MGB probes or Lion probes (Biotools), flourescent dyes such as SYBR Green I, SYBR Green II, SYBR gold, CellTracker Green, 7-AAD, ethidium homodimer I, ethidium homodimer II, ethidium homodimer III or ethidium bromide, epitope tags such as the FLAG or HA epitope, and enzyme tags such as alkaline phosphatase, horseradish peroxidase, $I^2$-galactosidase, alkaline phosphatase, β-galactosidase, or acetylcholinesterase and hapten conjugates such as digoxigenin or dinitrophenyl, or members of a binding pair that are capable of forming complexes such as streptavidin/biotin, avidin/biotin or an antigen/antibody complex including, for example, rabbit IgG and anti-rabbit IgG; fluorophores such as umbelliferone, fluorescein, fluorescein isothiocyanate, rhodamine, tetramethyl rhodamine, eosin, green fluorescent protein, erythrosin, coumarin, methyl coumarin, pyrene, malachite green, stilbene, lucifer yellow, Cascade Blue, dichlorotriazinylamine fluorescein, dansyl chloride, phycoerythrin, fluorescent lanthanide complexes such as those including Europium and Terbium, Cy3, Cy5, molecular beacons and fluorescent derivatives thereof, a luminescent material such as luminol; light scattering or plasmon resonant materials such as gold or silver particles or quantum dots; or radioactive material including $^{14}C$, $^{123}I$, $^{124}I$, $^{125}I$, $^{131}I$, $^{99m}Tc$, $^{35}S$ or $^{3}H$; or spherical shells, and probes labeled with any other signal generating label known to those of skill in the art. For example, detectable molecules include but are not limited to fluorophores as well as others known in the art as described, for example, in Principles of Fluorescence Spectroscopy, Joseph R. Lakowicz (Editor), Plenum Pub Corp, 2nd edition (July 1999) and the $6^{th}$ Edition of the Molecular Probes Handbook by Richard P. Hoagland.

Intercalating dyes are detected using the devices of the invention include but are not limited to phenanthridines and acridines (e.g., ethidium bromide, propidium iodide, hexidium iodide, dihydroethidium, ethidium homodimer-1 and -2, ethidium monoazide, and ACMA); some minor grove binders such as indoles and imidazoles (e.g., Hoechst 33258, Hoechst 33342, Hoechst 34580 and DAPI); and miscellaneous nucleic acid stains such as acridine orange (also capable of intercalating), 7-AAD, actinomycin D, LDS751, and hydroxystilbamidine. All of the aforementioned nucleic acid stains are commercially available from suppliers such as Molecular Probes, Inc.

Still other examples of nucleic acid stains include the following dyes from Molecular Probes: cyanine dyes such as SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red). Other detectable markers include chemiluminescent and chromogenic molecules, optical or electron density markers, etc.

As noted above in certain embodiments, labels comprise semiconductor nanocrystals such as quantum dots (i.e., Qdots), described in U.S. Pat. No. 6,207,392. Qdots are commercially available from Quantum Dot Corporation. The semiconductor nanocrystals useful in the practice of the invention include nanocrystals of Group II-VI semiconductors such as MgS, MgSe, MgTe, CaS, CaSe, CaTe, SrS, SrSe, SrTe, BaS, BaSe, BaTe, ZnS, ZnSe, ZnTe, CdS, CdSe, CdTe, HgS, HgSe, and HgTe as well as mixed compositions thereof; as well as nanocrystals of Group III-V semiconductors such as GaAs, InGaAs, InP, and InAs and mixed compositions thereof. The use of Group IV semiconductors such as germanium or silicon, or the use of organic semiconductors, may also be feasible under certain conditions. The semiconductor nanocrystals may also include alloys comprising two or more semiconductors selected from the group consisting of the above Group III-V compounds, Group II-VI compounds, Group IV elements, and combinations of same.

In addition to various kinds of fluorescent DNA-binding dye, other luminescent labels such as sequence specific probes can be employed in the amplification reaction to facilitate the detection and quantification of the amplified product. Probe based quantitative amplification relies on the sequence-specific detection of a desired amplified product. Unlike the dye-based quantitative methods, it utilizes a luminescent, target-specific probe (e.g., TaqMan® probes) resulting in increased specificity and sensitivity. Methods for performing probe-based quantitative amplification are well established in the art and are taught in U.S. Pat. No. 5,210,015.

In another embodiment fluorescent oligonucleotide probes are used to quantify the DNA. Fluorescent oligonucleotides (primers or probes) containing base-linked or terminally-linked fluors and quenchers are well-known in the art. They can be obtained, for example, from Life Technologies (Gaithersburg, Md.), Sigma-Genosys (The Woodlands, Tex.), Genset Corp. (La Jolla, Calif.), or Synthetic Genetics (San Diego, Calif.). Base-linked fluors are incorporated into the oligonucleotides by post-synthesis modification of oligonucleotides that are synthesized with reactive groups linked to bases. One of skill in the art will recognize that a large number of different fluorophores are available, including from commercial sources such as Molecular Probes, Eugene, Oreg. and other fluorophores are known to those of skill in the art. Useful fluorophores include: fluorescein, fluorescein isothiocyanate (FITC), carboxy tetrachloro fluorescein (TET), NHS-fluorescein, 5 and/or 6-carboxy fluorescein (FAM), 5-(or 6-) iodoacetamidofluorescein, 5-{[2(and 3)-5-(Acetylmercapto)-succinyl]amino}fluorescein (SAMSA-fluorescein), and other fluorescein derivatives, rhodamine, Lissamine rhodamine B sulfonyl chloride, Texas red sulfonyl chloride, 5 and/or 6 carboxy rhodamine (ROX) and other rhodamine derivatives, coumarin, 7-amino-methyl-coumarin, 7-Amino-4-methylcoumarin-3-acetic acid (AMCA), and other coumarin derivatives, BODIPY™ fluorophores, Cascade Blue™ fluorophores such as 8-methoxypyrene-1,3, 6-trisulfonic acid trisodium salt, Lucifer yellow fluorophores such as 3,6-Disulfonate-4-amino-naphthalimide, phycobiliproteins derivatives, Alexa fluor dyes (available from Molecular Probes, Eugene, Oreg.) and other fluorophores known to those of skill in the art. For a general listing of useful fluorophores, see also Hermanson, G. T., BIOCONJUGATE TECHNIQUES (Academic Press, San Diego, 1996).

Embodiments using fluorescent reporter probes produce accurate and reliable results. Sequence specific RNA or DNA based probes are used to specifically quantify the probe sequence and not all double stranded DNA. This also allows for multiplexing—assaying for several genes in the same reaction by using specific probes with different-colored labels.

In one embodiment PCR is carried out in a thermal cycler comprising a the liquid metal or thermally conductive fluid heat block comprising a liquid composition. In an embodiment, the thermal cycler further comprises an optical assembly. In another embodiment the liquid metal or thermally conductive fluid heat block rapidly and uniformly modulates the temperature of samples contained within sample vessels to allow detection of amplification products in real time. In another embodiment the detection is via a non-specific nucleic acid label such as an intercalating dye, wherein the signal index, or the positive fluorescence intensity signal generated by a specific amplification product is at least 3 times the fluorescence intensity generated by a PCR control sample, such as about 3.5, 4.5, 5, 5.5, 6, 6.5, 7, 7.5, 8, 8.5, 9, 9.5, 10, 10.5, or 11. In an embodiment the thermal cycler may modulate the sample temperature by more than 10° C. per second, such as 10.5° C. per second.

In one embodiment an RNA based probe with a fluorescent reporter and a quencher held in adjacent positions is used. The close proximity of the reporter to the quencher prevents its fluorescence, it is only after the breakdown of the probe that the fluorescence is detected. This process depends on the 5' to 3' exonuclease activity of the polymerase used in the PCR reaction cocktail.

Typically, the reaction is prepared as usual, with the addition of the sequence specific labeled probe the reaction commences. After denaturation of the DNA the labeled probe is able to bind to its complementary sequence in the region of interest of the template DNA. When the PCR reaction is heated to the proper extension temperature by the liquid metal or thermally conductive fluid block, the polymerase is activated and DNA extension proceeds. As the polymerization continues it reaches the labeled probe bound to the complementary sequence of DNA. The polymerase breaks the RNA probe into separate nucleotides, and separates the fluorescent reporter from the quencher. This results in an increase in fluorescence as detected by the optical assembly. As PCR progresses more and more of the fluorescent reporter is liberated from its quencher, resulting in a well defined geometric increase in fluorescence. This allows accurate determination of the final, and initial, quantities of DNA.

Diagnostic Use

In various applications, devices of the invention can be utilized for in vitro diagnostic uses, such as detecting infectious or pathogenic agents. In one embodiment, PCR is conducted using a device of the invention to detect various such agents, which can be any pathogen including without any limitation bacteria, yeast, fungi, virus, eukaryotic parasites, etc; infectious agent including influenza virus, parainfluenza virus, adenovirus, rhinovirus, coronavirus, hepatitis viruses A, B, C, D, E, etc, HIV, enterovirus, papillomavirus, coxsackievirus, herpes simplex virus, or Epstein-Barr virus; bacteria including *Mycobacterium, Streptococcus, Salmonella, Shigella, Staphylococcus, Neisseria, Pseudomonads, Clostridium*, or *E. coli*. It will be apparent to one of skill in the art that the PCR, sequencing reactions and related processes are readily adapted to the devices of the invention for use to detect any infectious agents.

One advantage of the devices of the invention is the capability to perform ultra fast PCR, which provides relatively faster times for diagnostic purposes. For some applications (e.g., detection of biothreat agents, intra-operative diagnostic testing), rapid PCR is a benefit. One important requirement for rapid real-time PCR are a thermal cycler that allows rapid heating, cooling, and thermal transfer, and a signal generation system that is compatible with the short cycle times associated with fast PCR. As described herein, the thermal cyclers of the invention can provide rapid cooling (e.g., 5-17° C./second) and rapid heating (e.g., 10-44° C./second). For example, the devices of the invention can provided cycle times as low as about 2 seconds if desired.

Furthermore, such ultra fast PCR processes can be conducted by coupling the devices of the invention with reagents known in the art to facilitate faster results, in both amplification and time required to produce a detectable signal. Such reagents are known in the art, such as disclosed in U.S. Patent Application No. 2005/0164219. One of these that we have used is a faster polymerase such as KOD.

For example, specialized labeled primers can provide signal generation that is instantaneous. (U.S. Patent Application No. 2005/0164219). A reaction that is extended in the previous cycle undergoes an internal rearrangement, and as soon as the extension temperature is reached, the signal is generated. In a standard PCR reaction with slow cycling conditions, this signal generation difference is not significant. However, when the extension times are reduced in rapid PCR, this feature becomes an advantage and translates into fast PCR. With the devices of the invention a single-copy bacterial sequences may be detected in less than 15 minutes. One example is the rapid detection of low levels of *Bacillus* spp using Scorpions primers and a fast PCR machine. Furthermore, depending on the amount of input DNA an infectious agent may be detected in less than 10 minutes, and even low levels could be detected in less than 14 minutes.

EXAMPLES

Example 1

Stainless Steel PCR Sample Vessels

Stainless steel PCR reaction sample vessels have been demonstrated as a suitable vessels in which to conduct polymerase chain reactions. The vessels used for initial tests were manufactured from stainless steel tubes with a final outer diameter of 0.061 inches. A two-inch length of sample vessel was closed at one end with a press-fit stainless steel plug.

Figure 12A:
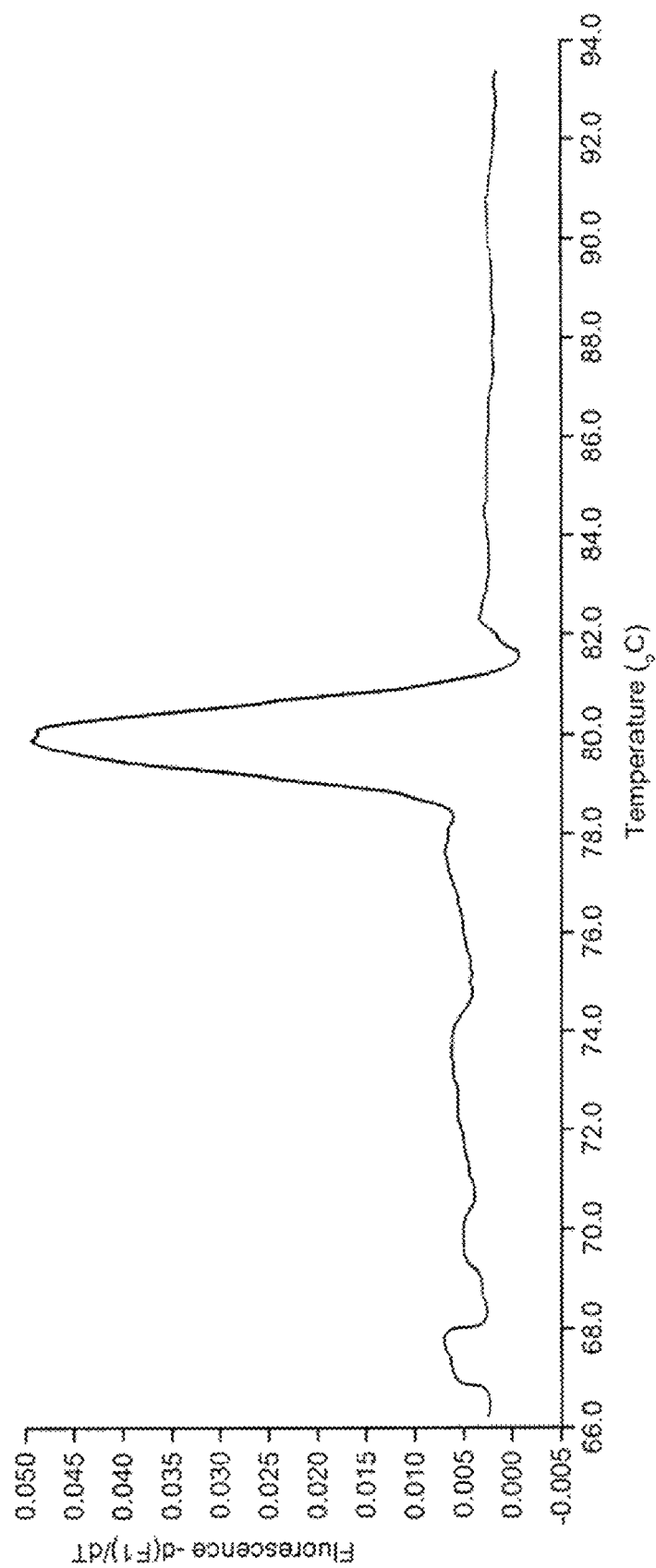
FIG. 12 illustrates melting curves from samples in which PCR amplification was performed inside a stainless steel sample vessel in comparison to a conventional glass capillary tube. The melt curve is nearly the same for both reactions, indicating a successful amplification. (A) Results from a PCR reaction performed in a conventional thermal cycler using metal sample vessels. PCR was carried out for 40 cycles then SYBR green was used to detect the production of a PCR amplicon. (B) Results from a PCR reaction performed in a conventional thermal cycler using commercially available sample vessels. PCR was carried out for 40 cycles then SYBR green was used to detect the production of a PCR amplicon.
Figure 12B:
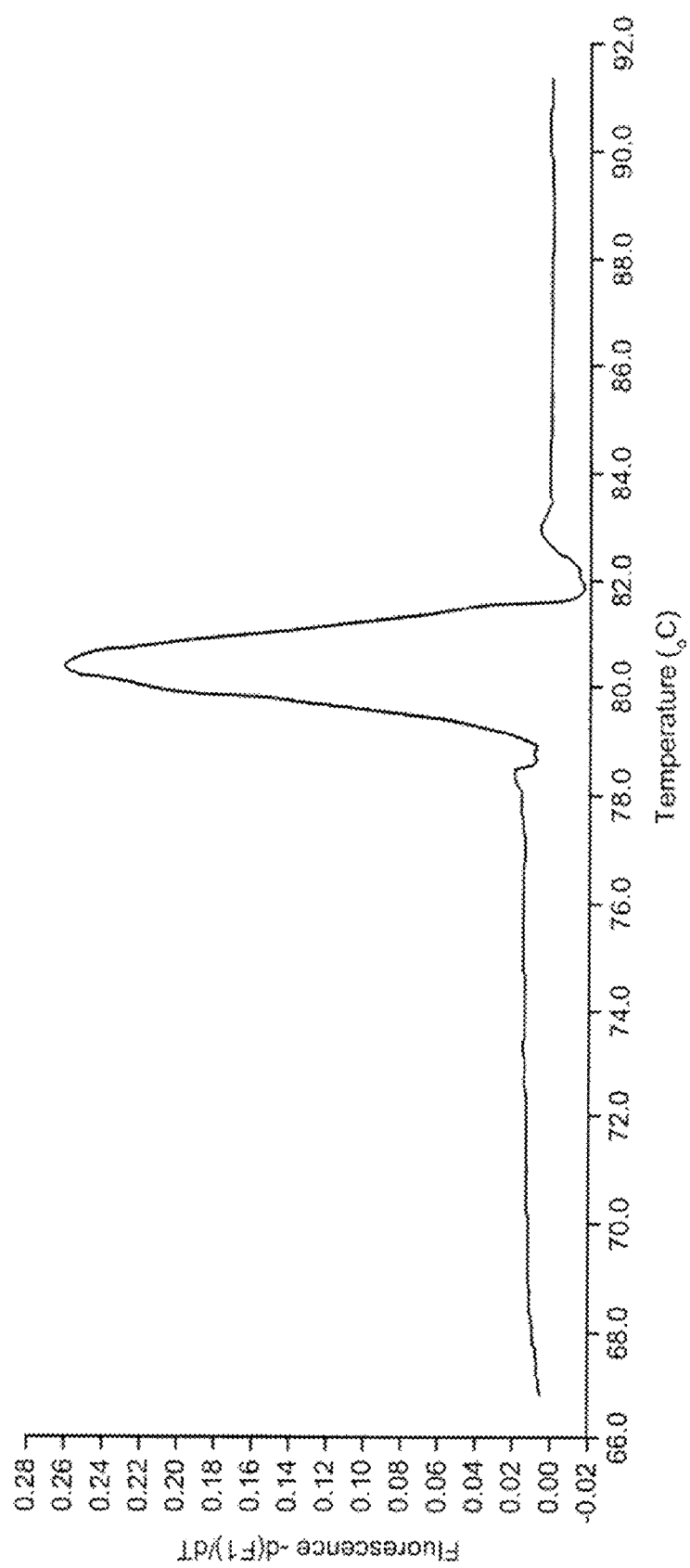

Identical 20 µL preparations for real time polymerase chain reactions using SYBR Green intercalating dye as an indicator were placed both in a commercial glass PCR capillary tube and in the metal sample vessel described above. The reagents were then sealed from outside air by floating 20 µL of mineral oil as an upper fluid layer in each vessel. These vessels were temperature cycled together in a commercial real-time PCR machine for 40 cycles, after which the contents of the metal sample vessel were transferred to a commercial glass PCR capillary tube. A melting curve was run on both samples, and the results indicate that PCR proceeded successfully in both the glass and metal vessels FIG. 12.

Example 2

Realtime PCR

The liquid metal or thermally conductive fluid heat block is well suited for real time PCR reactions because of the fast temperature ramping, thermal uniformity and reflectivity of the liquid metal or thermally conductive fluid.

Sample vessels are prepared by placing PCR reaction components into the sample vessels and sealing the vessels to prevent spillage or cross-contamination. The reaction components include buffer, target nucleic acid, appropriate primers and probes, nucleotides, polymerases, as well as optional additional components. In one embodiment, four fluorescent probes are included, each adapted to detect a different target sequence, and a particular reaction vessel may include any one or more of the fluorescent probes. Each probe advantageously responds to light of a different incident wavelength and emits light of a different wavelength.

A detection module is mounted above the heat block. The detection module includes four detection channels. Each channel is optimized for a different one of the fluorescent probes included in sample vessels. The sample vessels are placed into the heat block receptacle wells. The lid assembly is closed and positioned over the heat block.

Each channel of detection module is calibrated. Calibration is performed by operating stepper motors to position the detection module such that at least one of its channels is in optical communication with a calibration location. Each calibration location provides a known fluorescent response. Accordingly, calibration measurements can be used to correct subsequent sample measurements for variations or fluctuations in detector response. Numerous calibration techniques are known in the art. When a detection module with multiple channels is used, each channel may be independently calibrated.

A PCR cycle is performed. The thermal cycler controls the liquid metal or thermally conductive fluid heat block to regulate the temperature of the sample vessels thereby holding the sample vessels at desired temperatures for desired lengths of time to complete a two-step or three-step PCR cycle. The optical assembly scans and interrogates the sample vessels. The LED or other light source (such as a laser) for each channel is activated (flashed on for a brief period) to stimulate fluorescence. In one embodiment, the LEDs of different channels are operated in parallel; in an alternative embodiment, they are operated sequentially so as to avoid reflected LED light from one channel causing false signals in the photo detector of another channel. The operation of optical assembly may be controlled by an external computer or by a controller built into the thermal cycler. The measurements are synchronized with the operation of the thermal cycler, so that measurements are identifiable as corresponding to particular times in the PCR process. In another embodiment a controller component of the thermal cycler may automatically turn on and off one or more fans that are optionally attached to the thermal cycler or coupled to one or more heat sinks.

The resulting fluorescence is detected by the corresponding photodiode or other detector of the channel, which is read out to the external computer. The detectors may be read out in various ways. For instance, a peak signal may be detected, the signal may be integrated over a time interval, or the decay of the fluorescent signal after the LED has been deactivated may be measured.

These steps are repeated with the position of the detection module being changed each time so that each channel of detection module eventually interrogates each of the sample vessels. In one embodiment, scanning and interrogating four channels for each of 96 sample wells takes about 15 seconds. The external computer may execute a program that enables a user to view measurement data as they are collected, in graphical and/or tabular form.

The real-time fluorescence measurements from process are used to detect and quantify the presence of each target sequence. Such measurements may also be used for purposes such as determining reaction rates and adjusting reaction parameters for improved efficiency, as well as determining when additional reaction cycles are no longer needed in a particular experiment (e.g., when a sufficient quantity of a target sequence has been produced).

It will be appreciated that process is illustrative and that variations and modifications are possible. Steps described as sequential may be executed in parallel, order of steps may be varied, and steps may be modified or combined. For example, fluorescence measurements may be performed at any point during a PCR cycle, performed multiple times during each PCR cycle (including substantially continuous scanning of the sample wells), or not performed until after some number of PCR cycles. Any number of distinguishable fluorescent probes may be used in a single reaction vessel, and the detection module may be adapted to include at least as many channels as the number of probes in use. In some embodiments, the detection module includes multiple channels optimized for the same probe. This may reduce the scanning time since only one of these channels needs to be used to interrogate a particular sample well.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A thermal cycler apparatus comprising:
    a heat sink;
    a heating component in thermal contact with the heat sink, the heating component having a top surface;
    a closed bather sealing in a liquid composition, the closed bather having a top surface and a bottom surface, the top surface of the closed barrier having a plurality of wells configured to receive a plurality of sample vessels, wherein the wells extend into the liquid composition, and the bottom surface of the closed barrier being positioned in between the top surface of the closed barrier and the top surface of the heating component, the bottom surface of the closed barrier being in thermal contact with the top surface of the heating component; and
    a control assembly in communication with the heating component, the control assembly configured to cycle the temperature of samples in the plurality of sample vessels for nucleic acid amplification.

2. The apparatus of claim 1, wherein the bottom surface comprises a metal base plate.

3. The apparatus of claim 1, further comprising a sample plate including the plurality of sample vessels, each of the plurality of sample vessels having an open end, and the sample plate configured to be removably inserted into the plurality of wells.

4. The apparatus of claim 3, wherein at least one sample vessel comprises a reflective surface.

5. The apparatus of claim 3, further comprising a cap plate configured to cover the open ends of the plurality of sample vessels.

6. The apparatus of claim 5, wherein the cap plate comprises a plurality of extrusions removably inserted into the open ends of the sample vessels.

7. The apparatus of claim 6, wherein the plurality of extrusions comprise a light guide.

8. The apparatus of claim 1, wherein the liquid composition has a thermal conductivity of less than or equal to 8.0 W/m ° K.

9. The apparatus of claim 1, wherein the liquid composition has a thermal conductivity of less than or equal to 4.0 W/m ° K.

10. The apparatus of claim 1, further comprising at least one stirring element configured to actively mix the liquid composition.

11. The apparatus of claim 1, further comprising an optical assembly comprising a light emitter configured to direct light into the plurality of wells and an optical detector configured to detect light emitted from the samples.

12. The apparatus of claim 11, wherein the optical assembly further comprises:
    an excitation filter;
    a barrier filter; and
    a dichroic mirror configured to direct light from the light emitter passed through the excitation filter to the sample vessels and to direct light emitted from the samples to the optical detector via the barrier filter.

13. The apparatus of claim 11, wherein the optical assembly comprises a plurality of light emitters configured to emit light at different wavelengths.

14. The apparatus of claim 1, wherein the control assembly is configured to cycle the temperature of the samples such that the temperature between samples in any two sample vessels positioned in the plurality of wells has a variance of not more than +/−0.1° C.

15. The apparatus of claim 1, wherein the control assembly is configured to cycle the temperature of the samples such that the temperature of the samples has a variance from a desired temperature of not more than +/−0.1° C.

16. The apparatus of claim 1, wherein the control assembly is configured to cycle the temperature of the samples in sample vessels positioned in the plurality of wells such that the temperature of the samples remains at a temperature of at least 30° C. during nucleic acid amplification.

17. The apparatus of claim 1, wherein the heating component comprises a Peltier device.

18. The apparatus of claim 1, wherein control assembly is configured to cycle the temperature such that the heat block has a ramp rate of at least 5.0° C. per second.

19. A thermal cycler apparatus comprising:
- a heat block comprising a container sealing in a liquid having a first surface and a second surface opposite the first surface, the first surface comprising wells configured to receive sample vessels, wherein the wells extend into the liquid composition; and
- means for controlling the temperature of samples in the sample vessels for nucleic acid amplification, the means for controlling temperature comprising a heating component in thermal contact with the liquid, wherein the heating component has a heating surface in contact with the second surface of the heat block.

20. The apparatus of claim 19, wherein the liquid has a thermal conductivity of less than or equal to 6.0 W/m ° K.

21. The apparatus of claim 19, wherein the liquid has a thermal conductivity of less than or equal to 3.0 W/m ° K.

22. The apparatus of claim 19, wherein the container comprises a closed system with respect to the liquid.

23. The apparatus of claim 19, further comprising an optical assembly wherein the optical assembly comprises a light emitter configured to direct light into the wells and an optical detector configured to detect light emitted from the samples.

24. The apparatus of claim 23, wherein the optical assembly further comprises:
- an excitation filter;
- a barrier filter; and
- a dichroic mirror configured to direct light from the light emitter passed through the excitation filter to the sample vessels and to direct light emitted from the samples to the optical detector via the barrier filter.

25. The apparatus of claim 19, wherein the means for controlling temperature is configured to cycle the temperature of the samples such that the temperature between samples in any two sample vessels positioned in the wells has a variance of not more than +/−0.1° C.

26. The apparatus of claim 19, wherein the wells are made of a flexible material.

27. A thermal cycler apparatus comprising:
- a heat sink;
- a heating component in thermal contact with the heat sink;
- a closed barrier sealing in a liquid composition, the closed barrier having a top surface and a bottom surface, the top surface having a plurality of wells configured to receive a plurality of sample vessels, wherein the wells are made of a flexible material, wherein the wells extend into the liquid composition, and wherein the bottom surface is in thermal contact with the heating component; and
- a control assembly in communication with the heating component, the control assembly configured to cycle the temperature of samples in the plurality of sample vessels for nucleic acid amplification.

* * * * *